US012751823B2

(12) United States Patent
Bowe et al.

(10) Patent No.: US 12,751,823 B2
(45) Date of Patent: Oct. 6, 2026

(54) MECHANICAL GUIDES FOR PREFERENTIAL LEAFLET FOLDING DURING CRIMPING

(71) Applicant: Medtronic, Inc., Minneapolis, MN (US)

(72) Inventors: Jason Bowe, Blaine, MN (US); Matthew Genovese, Windsor, CA (US); Victoria Ung, Novato, CA (US); Jeffrey Sandstrom, Scandia, MN (US); Matthew Ziebol, Blaine, MN (US); Steven Claessens, Tualatin, OR (US); Radhika Bhargav, Mountain View, CA (US); Alkindi Kibria, Irvine, CA (US); Salvador O. Avelar, Santa Rosa, CA (US); Brian Castelli, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 936 days.

(21) Appl. No.: 17/957,943

(22) Filed: Sep. 30, 2022

(65) Prior Publication Data

US 2023/0139876 A1 May 4, 2023

Related U.S. Application Data

(60) Provisional application No. 63/274,622, filed on Nov. 2, 2021.

(51) Int. Cl.
*A61F 2/24* (2006.01)
*A61F 2/95* (2013.01)

(52) U.S. Cl.
CPC .......... *A61F 2/2427* (2013.01); *A61F 2/2418* (2013.01); *A61F 2/9522* (2020.05)

(58) Field of Classification Search
None
See application file for complete search history.

(56) References Cited

U.S. PATENT DOCUMENTS 3,571,886 A 3/1971 Corsmeier
5,810,873 A 9/1998 Morales
(Continued)

FOREIGN PATENT DOCUMENTS

EP 3995115 A1 5/2022

OTHER PUBLICATIONS

Extended European Search Report from corresponding European Patent Application No. 22204688.0, dated Mar. 3, 2023, 10 pgs.

*Primary Examiner* — Megan Y Wolf
(74) *Attorney, Agent, or Firm* — MEDLER FERRO WOODHOUSE & MILLS PLLC

(57) ABSTRACT

An assembly including a transcatheter valve prosthesis and a leaflet folding accessory configured for use when compressing the transcatheter valve prosthesis into the crimped configuration. The transcatheter valve prosthesis includes a frame and a prosthetic valve component including at least one leaflet disposed within and secured to the frame. The leaflet folding accessory includes a plurality of guide fingers. A leaflet contact portion of each guide finger is configured to be disposed radially within the frame and contact an inner surface of a leaflet of the at least one leaflet. During crimping of the transcatheter valve prosthesis, the plurality of guide fingers remain disposed radially within the frame such that the at least one leaflet preferentially folds around the plurality of guide fingers.

16 Claims, 19 Drawing Sheets

(56) References Cited

U.S. PATENT DOCUMENTS

| | | | |
|---|---|---|---|
| 8,608,770 | B2 | 12/2013 | Forster et al. |
| 9,265,607 | B2 | 2/2016 | Glazier |
| 9,757,232 | B2 | 9/2017 | Peterson et al. |
| 10,973,631 | B2 | 4/2021 | Scheinblum et al. |
| 11,446,470 | B2 | 9/2022 | Castelli et al. |
| 2008/0154335 | A1 | 6/2008 | Benichou et al. |
| 2018/0133000 | A1 | 5/2018 | Scheinblum et al. |
| 2021/0275298 | A1 | 9/2021 | Peterson et al. |
| 2022/0039979 | A1 | 2/2022 | Castelli et al. |
| 2022/0054264 | A1 | 2/2022 | Mcguinn et al. |
| 2022/0142771 | A1* | 5/2022 | Menon .................. A61F 2/2427 |

* cited by examiner

MECHANICAL GUIDES FOR PREFERENTIAL LEAFLET FOLDING DURING CRIMPING

CROSS-REFERENCE TO RELATED APPLICATIONS

This application claims the benefit of U.S. Provisional Application No. 63/274,622, filed Nov. 2, 2021, the entire content of which is incorporated herein by reference.

FIELD

The present technology is generally related to prosthetic valve devices, and in particular is directed to a leaflet folding accessory for use when radially compressing the prosthetic valve device into a crimped configuration.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position.

The present disclosure relates to improvements in radially compressing or crimping a heart valve prosthesis to ensure that the heart valve prosthesis has a low profile for transcatheter delivery through a patient's vasculature and further to ensure that the leaflets of the heart valve prosthesis are not damaged during crimping.

SUMMARY

According to a first embodiment hereof, the present disclosure provides an assembly including a transcatheter valve prosthesis and a leaflet folding accessory. The transcatheter valve prosthesis includes a frame and a prosthetic valve component including at least one leaflet disposed within and secured to the frame. The transcatheter valve prosthesis has an expanded configuration and a crimped configuration for delivery within a vasculature. The leaflet folding accessory is configured for use when compressing the transcatheter valve prosthesis into the crimped configuration. The leaflet folding accessory includes a plurality of guide fingers. A leaflet contact portion of each guide finger is configured to be disposed radially within the frame and contact an inner surface of a leaflet of the at least one leaflet. During crimping of the transcatheter valve prosthesis, the plurality of guide fingers are configured to remain disposed radially within the frame such that the at least one leaflet preferentially folds around the plurality of guide fingers.

In an aspect of the first embodiment, and in combination with any other aspects herein, the disclosure provides that the plurality of guide fingers include at least three guide fingers.

In an aspect of the first embodiment, and in combination with any other aspects herein, the disclosure provides that the plurality of guide fingers include exactly three guide fingers and the prosthetic valve component includes exactly three leaflets.

In an aspect of the first embodiment, and in combination with any other aspects herein, the disclosure provides that the plurality of guide fingers are configured so as to not directly contact an outer surface of the at least one leaflet.

In an aspect of the first embodiment, and in combination with any other aspects herein, the disclosure provides each guide finger is formed of a pliable polymer material.

In an aspect of the first embodiment, and in combination with any other aspects herein, the disclosure provides that the plurality of guide fingers are circumferentially spaced apart from each other.

In an aspect of the first embodiment, and in combination with any other aspects herein, the disclosure provides that the leaflet folding accessory includes a handle configured to be held by a user. The handle is attached to a first end of each guide finger.

In an aspect of the first embodiment, and in combination with any other aspects herein, the disclosure provides that the leaflet folding accessory further includes a collar disposed over the handle. The collar is moveable relative to the guide fingers in order to adjust a radial position of the leaflet contact portions of the guide fingers.

In an aspect of the first embodiment, and in combination with any other aspects herein, the disclosure provides that each guide finger includes an outward bump formed on a midportion thereof, the outward bump extending radially outward and being configured to interact with the collar.

In an aspect of the first embodiment, and in combination with any other aspects herein, the disclosure provides that the leaflet contact portion of each guide finger is a curved end portion.

In an aspect of the first embodiment, and in combination with any other aspects herein, the disclosure provides that each guide finger is a rod having a substantially circular cross section.

In an aspect of the first embodiment, and in combination with any other aspects herein, the disclosure provides that each guide finger tapers from a first end to a second end thereof, the first end having a greater diameter than the second end.

In an aspect of the first embodiment, and in combination with any other aspects herein, the disclosure provides that each guide finger has a flattened, ribbon-like cross section.

In an aspect of the first embodiment, and in combination with any other aspects herein, the disclosure provides that the leaflet folding accessory includes a handle configured to be held by a user and wherein a first end of each guide finger is attached to a nut, the nut being removably attached to an end of the handle.

In an aspect of the first embodiment, and in combination with any other aspects herein, the disclosure provides that the assembly further includes a valve seat locator configured to receive an end of the transcatheter valve prosthesis. The valve seat locator is configured to align the leaflet contact portion of each guide finger with a midline of the at least one leaflet.

In an aspect of the first embodiment, and in combination with any other aspects herein, the disclosure provides that the leaflet folding accessory includes a hub. The hub is attached to a first end of each guide finger, and a second end of each guide finger is unconstrained. In an embodiment, the hub includes a plurality of slots formed on an outer surface thereof, each slot being configured to receive one of the guide fingers of the plurality of guide fingers. The slots permit only radial movement of the guide fingers during crimping of the transcatheter valve prosthesis. In an embodiment, the leaflet folding accessory also includes a slotted tubular component extending axially from the hub and includes a plurality of second slots on an outer surface thereof, each second slot being configured to receive one of the guide fingers of the plurality of guide fingers. The guide fingers radially collapse into the second slots during crimping of the transcatheter valve prosthesis.

In an aspect of the first embodiment, and in combination with any other aspects herein, the disclosure provides that a first end of each guide finger is attached to a first hub and a second end of each guide finger is attached to a second hub. The second hub includes a lumen longitudinally extending therethrough such that the second hub is configured to be slide relative to an outer surface of a delivery system.

According to a second embodiment hereof, the present disclosure provides a method of crimping a transcatheter valve prosthesis onto a delivery system. A leaflet folding accessory is positioned at least partially within a transcatheter valve prosthesis. The leaflet folding accessory includes a plurality of guide fingers, each guide finger having a leaflet contact portion. The transcatheter valve prosthesis includes a frame and a prosthetic valve component including at least one leaflet disposed within and secured to the frame. The transcatheter valve prosthesis is in an expanded configuration, and the leaflet folding accessory is positioned such that the leaflet contact portion of each guide finger is disposed radially within the frame and contacts an inner surface of a leaflet of the at least one leaflet. A crimper is positioned over the transcatheter valve prosthesis in the expanded configuration. A delivery system is positioned through a central lumen of the transcatheter valve prosthesis. The crimper is operated to compress the transcatheter valve prosthesis into at least a partially crimped configuration, and the leaflet folding accessory remains positioned such that each guide finger is disposed radially within the frame such that the at least one leaflet preferentially folds around the plurality of guide fingers. The leaflet folding accessory from is removed within the transcatheter valve prosthesis after the step of operating the crimper to compress the transcatheter valve prosthesis into at least the partially crimped configuration.

In an aspect of the second embodiment, and in combination with any other aspects herein, the disclosure provides the step of operating the crimper to compress the transcatheter valve prosthesis into a fully crimped configuration after the step of removing the leaflet folding accessory from within the transcatheter valve prosthesis.

In an aspect of the second embodiment, and in combination with any other aspects herein, the disclosure provides the step of twisting the leaflet folding tool prior to the step of removing the leaflet folding accessory from within the transcatheter valve prosthesis. The step of twisting the leaflet folding tool may occur during or after the step of operating the crimper to compress the transcatheter valve prosthesis into at least the partially crimped configuration.

In an aspect of the second embodiment, and in combination with any other aspects herein, the disclosure provides the step of positioning a leaflet folding accessory at least partially within a transcatheter valve prosthesis includes aligning each guide finger with a midline of a leaflet of the at least one leaflet.

In an aspect of the second embodiment, and in combination with any other aspects herein, the disclosure provides that the frame includes a plurality of commissure posts and a plurality of axial struts, each axial strut being circumferentially disposed between a pair of commissure posts. The midline of the at least one leaflet is aligned with an axial strut of the plurality of axial struts.

In an aspect of the second embodiment, and in combination with any other aspects herein, the disclosure provides that the step of positioning a leaflet folding accessory at least partially within a transcatheter valve prosthesis includes deflecting the leaflet contact portion of the guide fingers radially inwards.

In an aspect of the second embodiment, and in combination with any other aspects herein, the disclosure provides that the leaflet contact portion of the guide fingers are deflected radially inwards by rotating a collar to advance the collar relative to the guide fingers.

In an aspect of the second embodiment, and in combination with any other aspects herein, the disclosure provides that the step of positioning a leaflet folding accessory at least partially within a transcatheter valve prosthesis includes positioning an end of the transcatheter valve prosthesis into a valve seat locator such that each guide finger aligns with a midline of a leaflet of the at least one leaflet.

In an aspect of the second embodiment, and in combination with any other aspects herein, the disclosure provides that the plurality of guide fingers include at least three guide fingers.

In an aspect of the second embodiment, and in combination with any other aspects herein, the disclosure provides that the plurality of guide fingers include exactly three guide fingers and the prosthetic valve component includes exactly three leaflets. The step of positioning a leaflet folding accessory at least partially within a transcatheter valve prosthesis includes positioning one guide finger to contact a single leaflet.

In an aspect of the second embodiment, and in combination with any other aspects herein, the disclosure provides that the plurality of guide fingers do not directly contact an outer surface of the at least one leaflet during the step of operating the crimper to compress the transcatheter valve prosthesis into at least the partially crimped configuration.

In an aspect of the second embodiment, and in combination with any other aspects herein, the disclosure provides each guide finger is formed of a pliable polymer material.

In an aspect of the second embodiment, and in combination with any other aspects herein, the disclosure provides that the plurality of guide fingers are circumferentially spaced apart from each other.

In an aspect of the second embodiment, and in combination with any other aspects herein, the disclosure provides that the leaflet folding accessory includes a handle configured to be held by a user, the handle being attached to a first end of each guide finger.

In an aspect of the second embodiment, and in combination with any other aspects herein, the disclosure provides that the leaflet contact portion of each guide finger is a curved end portion.

In an aspect of the second embodiment, and in combination with any other aspects herein, the disclosure provides each guide finger is a rod having a substantially circular cross section.

In an aspect of the second embodiment, and in combination with any other aspects herein, the disclosure provides that each guide finger tapers from a first end to a second end thereof, the first end having a greater diameter than the second end.

In an aspect of the second embodiment, and in combination with any other aspects herein, the disclosure provides that each guide finger has a flattened, ribbon-like cross section.

In an aspect of the second embodiment, and in combination with any other aspects herein, the disclosure provides that the leaflet folding accessory includes a hub, the hub being attached to a first end of each guide finger, and a second end of each guide finger is unconstrained.

In an aspect of the second embodiment, and in combination with any other aspects herein, the disclosure provides that the hub includes a plurality of slots formed on an outer surface thereof, each slot being configured to receive one of the guide fingers of the plurality of guide fingers. The slots permit only radial movement of the guide fingers during the step of operating the crimper to compress the transcatheter valve prosthesis into at least the partially crimped configuration. In an embodiment, the leaflet folding accessory also includes a slotted tubular component extending axially from the hub and includes a plurality of second slots on an outer surface thereof, each second slot being configured to receive one of the guide fingers of the plurality of guide fingers. The guide fingers radially collapse into the second slots during the step of operating the crimper to compress the transcatheter valve prosthesis into at least the partially crimped configuration.

In an aspect of the second embodiment, and in combination with any other aspects herein, the disclosure provides a first end of each guide finger is attached to a first hub and a second end of each guide finger is attached to a second hub. The second hub includes a lumen longitudinally extending therethrough such that the second hub is configured to be slide relative to an outer surface of a delivery system.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "inflow" and "outflow", when used in the following description to refer to a native vessel, native valve, or a device to be implanted into a native vessel or native valve, such as a transcatheter valve prosthesis, are with reference to the direction of blood flow. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention of the application and uses of the invention. Furthermore, there is no intention to be bound by any expressed or implied theory presented in the preceding field of the invention, background, summary or the following detailed description.

Embodiments hereof relate to a leaflet folding accessory or tool configured for use with a transcatheter valve prosthesis when radially compressing the transcatheter valve prosthesis from an expanded configuration into a crimped configuration for delivery within a vasculature. The folding pattern of the leaflets when the transcatheter valve prosthesis is in the crimped configuration determines the distribution of stresses and strains in the leaflets. During crimping of the transcatheter valve prosthesis, the crimping may cause leaflet damage and/or the leaflets may fold into an irregular pattern that adversely affects the profile of the transcatheter valve prosthesis in the crimped configuration. Embodiments of the leaflet folding accessory described herein are configured to guide or control folding of the leaflets of the transcatheter valve prosthesis during crimping, thereby preventing undesirable folding and/or damage to the leaflets during crimping. The leaflets preferentially fold in a predetermined and desirable pattern which results in a smaller delivery profile of the transcatheter valve prosthesis for delivery. As a result, the leaflet folding accessories described herein increase the packing efficiency of the transcatheter valve prosthesis. The leaflet folding accessory tool is removed after the transcatheter valve prosthesis is partially crimped or fully crimped but before the transcatheter valve prosthesis is delivered within a vasculature.

Figure 1A:
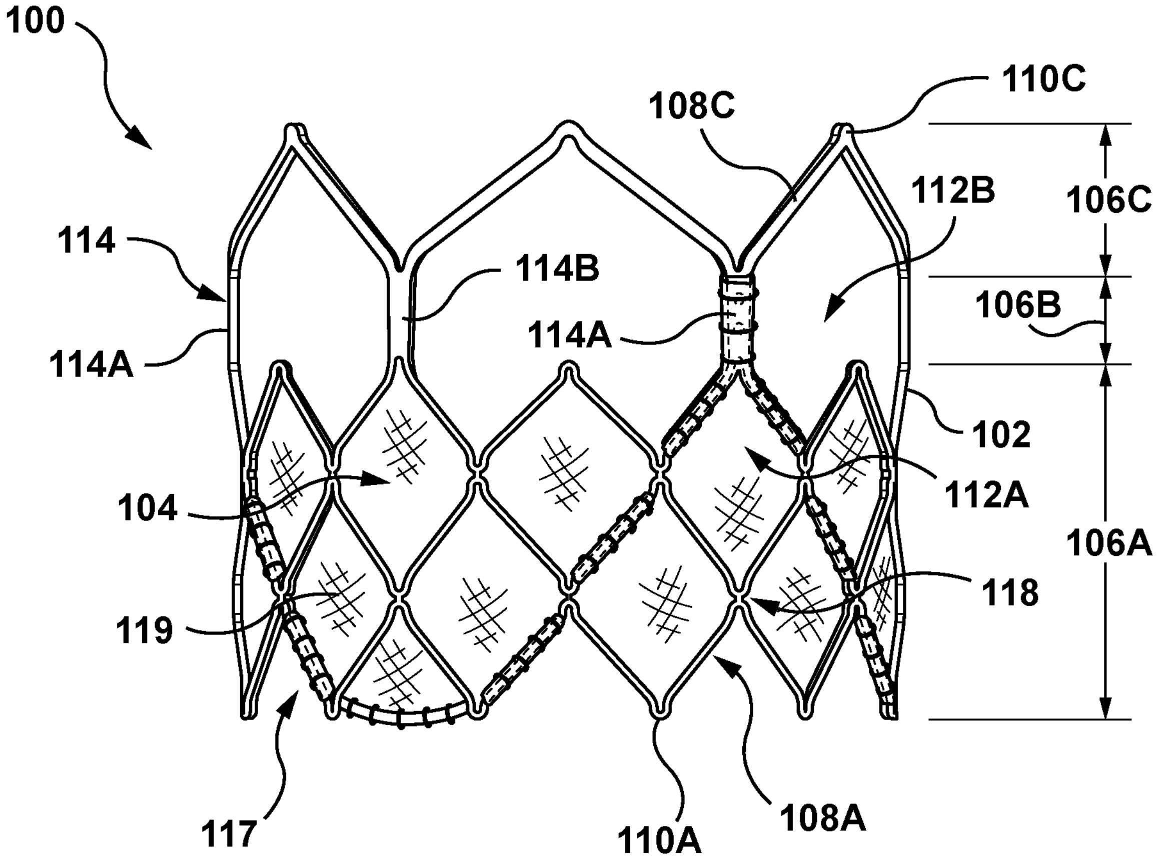
FIG. 1A depicts a side view of a transcatheter valve prosthesis according to embodiments thereof.
Figure 1B:
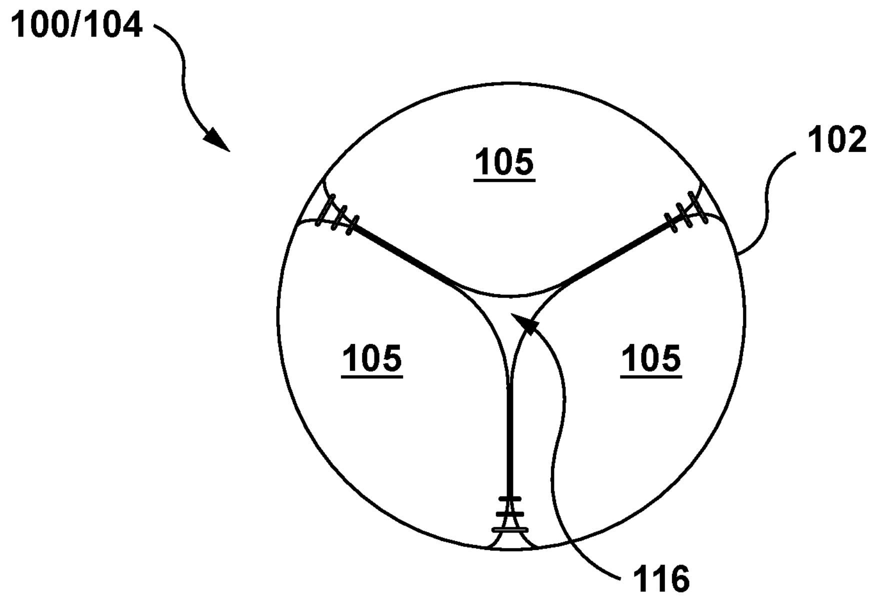
FIG. 1B depicts a top view of the transcatheter valve prosthesis of FIG. 1A.

FIGS. 1A and 1B illustrate a transcatheter valve prosthesis 100 that may be utilized with the embodiments of the crimping accessory described herein. The transcatheter valve prosthesis 100 is illustrated herein in order to facilitate description of the present invention. The following description of the transcatheter valve prosthesis 100 is merely exemplary in nature and is not intended to limit the invention or the application and uses of the invention. It is understood that any number of alternate heart valve prostheses can be used with the leaflet accessory tools and methods described herein. Other non-limiting examples of transcatheter valve prostheses that can be used with the leaflet accessory tools described herein are described in U.S. patent application Ser. No. 17/186,485, filed Feb. 26, 2021, which is incorporated by reference herein in its entirety. Although the transcatheter valve prosthesis 100 is a balloon-expandable heart valve prosthesis configured for placement within an aortic heart valve, embodiments of the crimping accessory described herein may be utilized with any transcatheter valve prosthesis that is crimped onto a delivery system. For example, embodiments of the leaflet folding accessory described herein may be utilized with a transcatheter heart valve configured for placement within a pulmonary, aortic, mitral, or tricuspid valve, or may be utilized with a transcatheter valve prosthesis configured for placement within a venous valve or within other body passageways where it is deemed useful. Embodiments of the leaflet folding accessory described herein may be utilized with a self-expanding transcatheter valve prosthesis or a balloon-expandable transcatheter valve prosthesis. There is no intention to be bound by any expressed or implied theory presented in the preceding technical field, background, brief summary or the following detailed description.

FIGS. 1A and 1B illustrate side and top views, respectively, of the transcatheter valve prosthesis 100. The transcatheter valve prosthesis 100 includes a radially-expandable frame 102 and a prosthetic valve component 104. The frame 102 of the transcatheter valve prosthesis 100 is a unitary frame or scaffold that supports the valve component 104 within the interior of the frame 102. In an embodiment, the frame 102 is balloon-expandable. The valve component 104 includes at least one leaflet 105 disposed within and secured to the frame 102. In an embodiment, the valve component 104 of the transcatheter valve prosthesis 100 includes exactly three leaflets 105, as shown in FIG. 1B. The valve component 104 of the transcatheter valve prosthesis 100 is capable of blocking flow in one direction to regulate flow there-through via the valve leaflets 105. The transcatheter valve prosthesis 100 has a crimped configuration for delivery within a vasculature and an expanded configuration (as shown in FIGS. 1A and 1B) for deployment within a native heart valve.

The frame 102 includes an inflow portion 106A, an outflow portion 106C, and a transition portion 106B bridging, connecting, or otherwise extending between the inflow portion 106A and the outflow portion 106C. The inflow portion 106A includes a plurality of crowns 110A and a plurality of struts 108A with each crown 110A being formed between a pair of opposing struts 108A. Each crown 110A is a curved segment or bend extending between opposing struts 108A. The inflow portion 106A is tubular, with a plurality of side openings 112A being defined by the plurality of crowns 110A and the plurality of struts 108A. In an embodiment, the plurality of side openings 112A may be diamond-shaped.

The outflow portion 106C includes a plurality of crowns 110C and a plurality of struts 108C with each crown 110C being formed between a pair of opposing struts 108C. Each crown 110C is a curved segment or bend extending between opposing struts 108C. The outflow portion 106C can be configured in a shape that forms a central lumen or passageway, for example, a ring.

The transition portion 106B bridges, connects, or otherwise extends between the inflow portion 106A and the outflow portion 106C. The transition portion 106B includes a total of six axial frame members 114, each axial frame member 114 extending between a crown 110C of the outflow portion 106C and a crown 110A of the inflow portion 106A. The axial frame members 114 are substantially parallel to the central longitudinal axis of the frame 102. Three of the six axial frame members 114 are commissure posts 114A and aligned with and attached to a respective commissure of the three leaflets 105 of the valve component 104. Three of the axial frame members 114 are axial struts 114B and are disposed between adjacent commissure posts 114A such that the axial struts 114B and the commissure posts 114A alternate around a circumference of the frame 102.

The frame 102 includes a plurality of endmost outflow side openings or cells 112B. The endmost outflow side openings 112B of the outflow portion 106C are relatively larger than the plurality of side openings 112A of the inflow portion 106A to improve access to the coronary arteries. More particularly, the endmost outflow side openings 112B of the outflow portion 106C are configured to be of sufficient size to be easily crossed with a coronary guide catheter into either the right coronary artery or the left main coronary artery once the transcatheter heart valve 100 is deployed in situ.

The valve component 104 of the transcatheter valve prosthesis 100 is capable of regulating flow therethrough via valve leaflets 105 that may form a replacement valve. FIGS. 1A and 1B illustrate an exemplary valve component 104 having three leaflets 105, although a single leaflet or bicuspid leaflet configuration may alternatively be used in embodiments hereof. FIG. 1A depicts a side view of the transcatheter valve prosthesis 100, with the valve component 104 being shown disposed within and secured to the frame 102 of the heart valve prosthesis 100. FIG. 1B depicts an atrial or inflow end view of the transcatheter valve prosthesis 100. When deployed in situ, the valve component 104 in a closed state is configured to block blood flow in one direction to regulate blood flow through a central lumen 116 of the frame 102 of the transcatheter valve prosthesis 100. The valve component 104 includes three valve leaflets 105 that open during diastole.

The frame 102 is configured to secure the valve component 104 within the central lumen 116 of the frame 102 and to secure the transcatheter valve prosthesis 100 in place in the vasculature of the patient. The three leaflets 105 of the valve component 104 are attached to the frame 102 along a margin of attachment 117 that follows struts 108A and nodes 118 of the inflow portion 106A of the frame 102. A node 118 is defined as a region where two crowns of the plurality of crowns 110A within the inflow portion 106A connect.

The valve component 104 further includes a graft material or skirt 119 which encloses or lines the inflow portion 106A of the frame 102 as would be known to one of ordinary skill in the art of prosthetic tissue valve construction, for example, using sutures or a suitable biocompatible adhesive. The leaflets 105 are attached to the skirt 119. Leaflets 105 are sutured or otherwise securely and sealingly attached along their bases to the interior surface of the skirt 119, or otherwise attached to the frame 102. Adjoining pairs of leaflets are attached to one another at their lateral ends to form commissures, with free edges of the leaflets 105 forming coaptation edges that meet in a closed configuration. The orientation of the leaflets 105 within the valve component 104 depends upon on which end of the transcatheter valve prosthesis 100 is the inflow end and which end of the transcatheter valve prosthesis 100 is the outflow end, thereby ensuring one-way flow of blood through the transcatheter valve prosthesis 100.

The valve leaflets 105 and the skirt 119 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

A crimper may be used to radially compress the transcatheter valve prosthesis 100 from an expanded configuration to a crimped configuration on a balloon of a delivery system for delivery within a vasculature. During the crimping process, the leaflets 105 of the valve component 104 may protrude or extend through the side openings 112B of the frame 102, and, as a result, become pinched therein. This may lead to damage of the leaflets 105, such as splitting, peeling, experiencing partial or full cuts, or separation of the layers of material. Each of these types of damages is considered unacceptable and may render the entire transcatheter valve prosthesis defective. Further, even if the leaflets 105 are not damaged as described above, they may still extend through the side openings 112B of the frame 102 resulting in the leaflets 105 protruding radially outside of the frame 102. If protruded, the leaflets 105 may extend radially far enough to exceed the profile tolerance of the transcatheter valve prosthesis 100, which may undesirably increase a crossing profile of the transcatheter valve prosthesis 100. Therefore, there exists a need to ensure the valve component 104 is maintained within the frame 102 during the crimping process.

Figure 2:
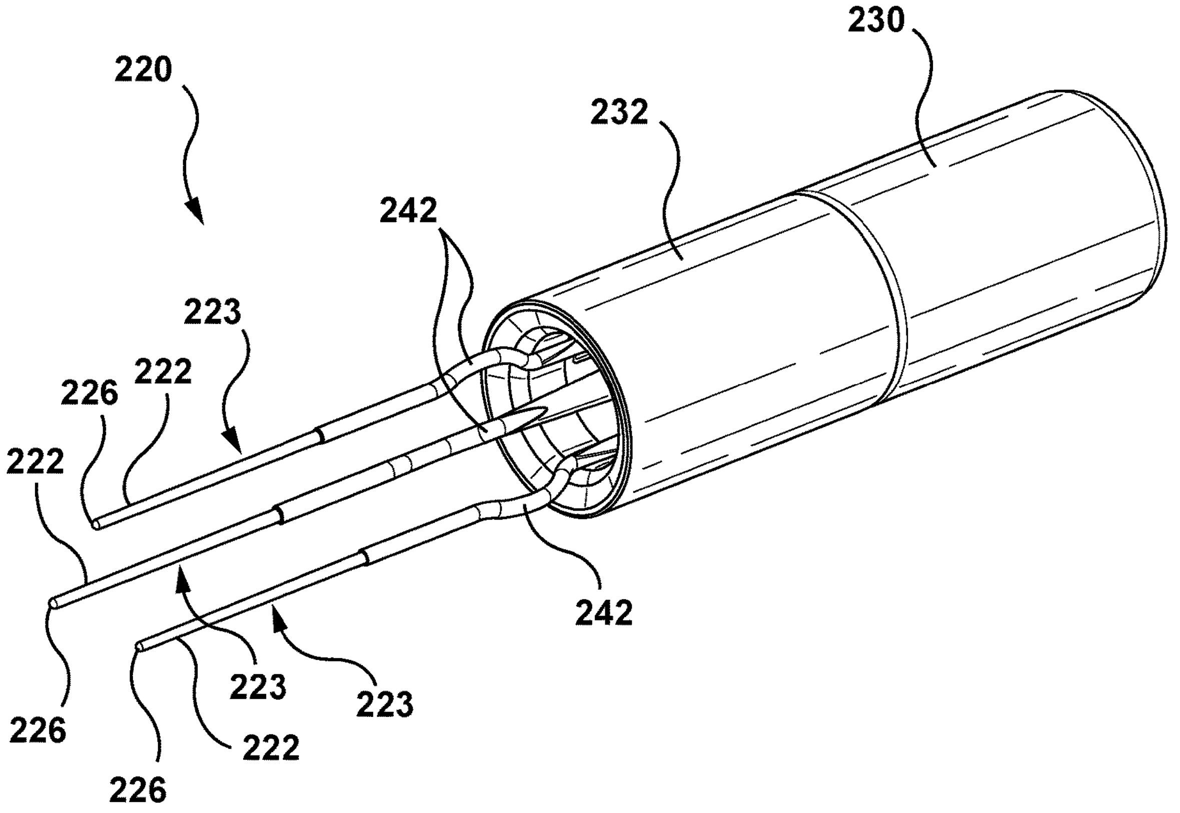
FIG. 2 depicts a perspective view of a leaflet folding accessory according to an embodiment hereof, wherein guide fingers of the leaflet folding accessory are in a leaflet contact configuration.

FIG. 2 depicts a perspective view of a leaflet folding accessory 220 according to an embodiment hereof. The leaflet folding accessory 220 is a mechanical guide or tool that is configured for use with a transcatheter valve prosthesis (such as but not limited to the transcatheter valve prosthesis 100) when radially compressing the transcatheter valve prosthesis into a crimped configuration for delivery within a vasculature. For illustrative purposes only, the leaflet folding accessory 220 will be described for use with the transcatheter valve prosthesis 100 since the structure thereof has been described herein.

The leaflet folding accessory 220 includes a plurality of guide fingers 222, a hub or handle 230, and a rotatable collar 232. In FIG. 2, the guide fingers 222 are depicted in a leaflet contact configuration in which a leaflet contact portion 223 of each guide finger 222 is configured and sized to be disposed radially within the frame 102 of the transcatheter valve prosthesis 100 and contact an inner surface of the leaflets 105. During crimping of the transcatheter valve prosthesis 100, the plurality of guide fingers 222 remain disposed radially within the frame 102 such that the leaflets 105 of the valve component 104 preferentially fold around the plurality of guide fingers 222. The leaflet contact portion 223 of each guide finger 222 holds at least a portion of a leaflet 105 of the transcatheter valve prosthesis 100 directly adjacent to or against an inner surface of the frame 105 of the transcatheter valve prosthesis 100 when the transcatheter valve prosthesis 100 is compressed into the crimped configuration. The guide fingers 222 are configured to contact only the inner surfaces of the leaflets 105 of the valve component 104. Stated another way, all of the guide fingers 222 are radially disposed entirely within the leaflets 105 of the valve component 104 and are configured such that the guide fingers 222 do not directly contact the outer surface of the leaflets 105 and do not directly contact the frame 102 of the transcatheter valve prosthesis 100.

As the transcatheter valve prosthesis 100 is crimped into a radially compressed configuration, the plurality of guide fingers 222 hold the leaflets 105 against an inner surface of the frame 105 of the transcatheter valve prosthesis 100 in order to cause the leaflets 105 to preferentially fold around the guide fingers 222. Stated another way, due to the presence of the guide fingers 222, the leaflets 105 fold into a predetermined pattern during crimping of the transcatheter valve prosthesis 100 which prevents any leaflet damage and/or irregular folding patterns that adversely affect the delivery profile of the transcatheter valve prosthesis 100. More particularly, without leaflet folding accessory 220, the leaflets 105 may fold inwards at different rates and thereby result in folding into an irregular pattern. For example, a single leaflet 105 may drop or fold prior to the remaining leaflet(s) 105 and such an inconsistent sequence may result in crimping the initially folded leaflet 105 more than the other leaflet(s) 105. Such different folding rates of the leaflets 105 may result in damage of the initially folded leaflet 105. However, when all the leaflets 105 are held in a defined pattern via the plurality of guide fingers 222, each leaflet 105 folds at a consistent rate and in a consistent pattern with each other leaflet 105, thereby allowing more packing of the leaflet material without damaging any leaflet.

In an embodiment, the plurality of guide fingers 222 cause the leaflets 105 to fold into a predetermined pattern that includes alternating folds or pleats (i.e., infolds and outfolds) that form around the plurality of guide fingers 222 during crimping. The predetermined pleated pattern of the leaflets 105 enables a smaller delivery profile or diameter of the transcatheter valve prosthesis 100 in the crimped configuration, and further the predetermined pleated pattern includes a controlled distribution of stresses and strains in the leaflets 105. The pleats or folds may be uniform in size and shape, or in another embodiment, the pleats may not be uniform in size and/or shape.

Figure 3:
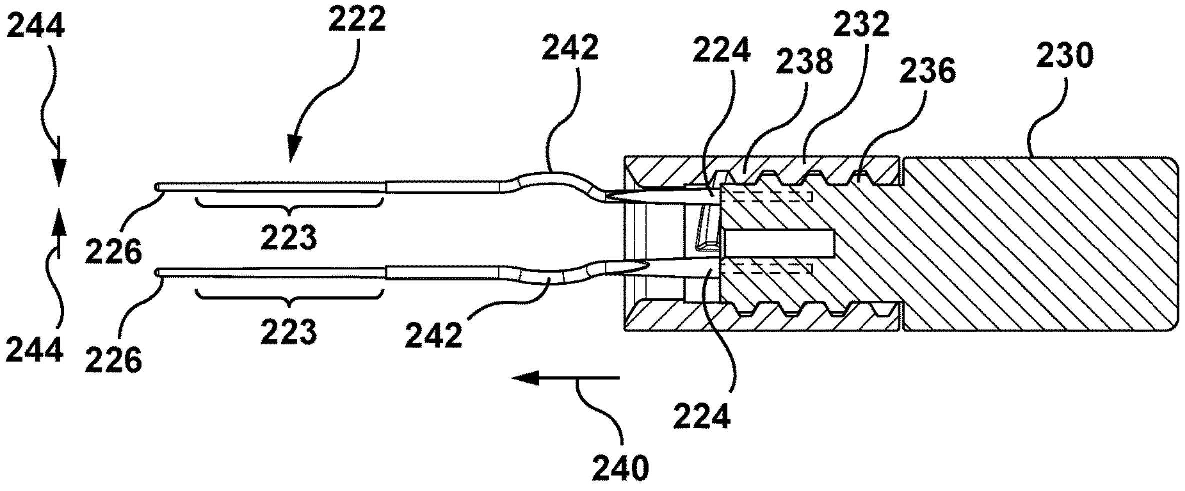
FIG. 3 depicts a sectional side view of the leaflet folding accessory of FIG. 2, wherein guide fingers of the leaflet folding accessory are in the leaflet contact configuration.
Figure 4:
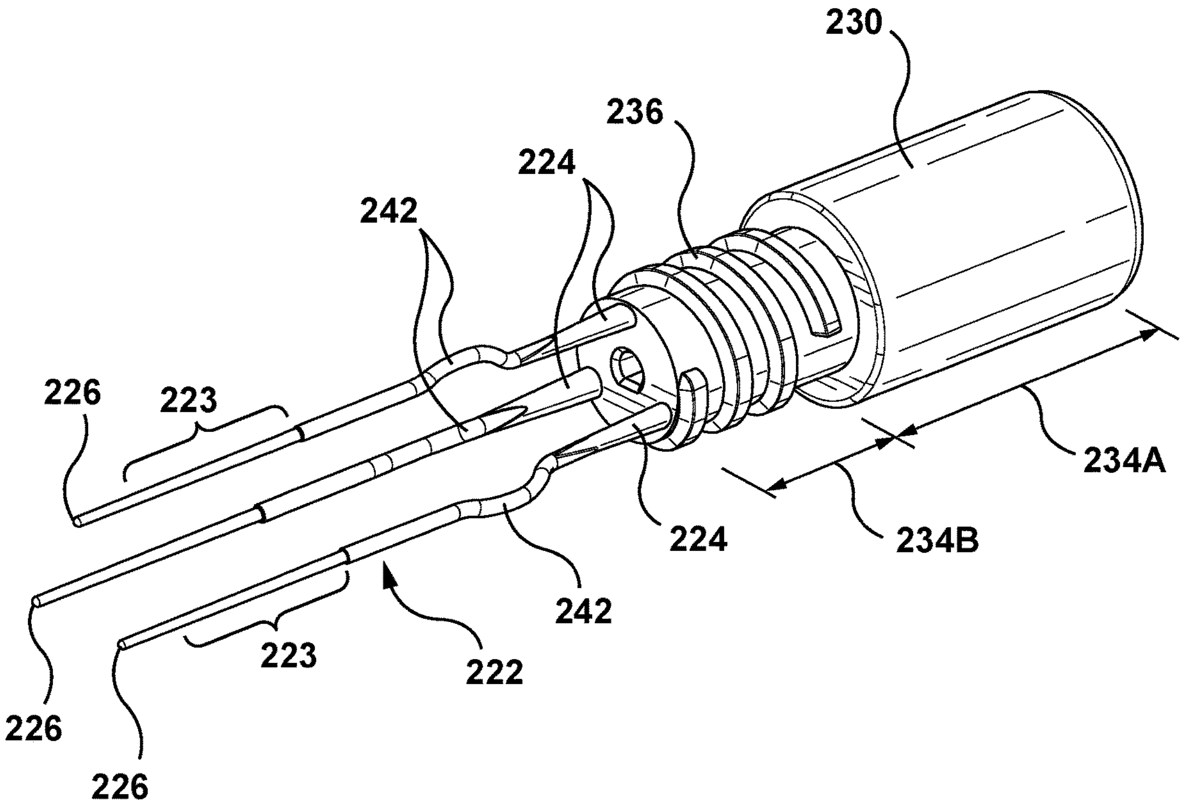
FIG. 4 depicts a perspective view of the leaflet folding accessory of FIG. 2, wherein guide fingers of the leaflet folding accessory are in the leaflet contact configuration and a collar of the leaflet folding accessory is removed for sake of illustration only.
Figure 5:
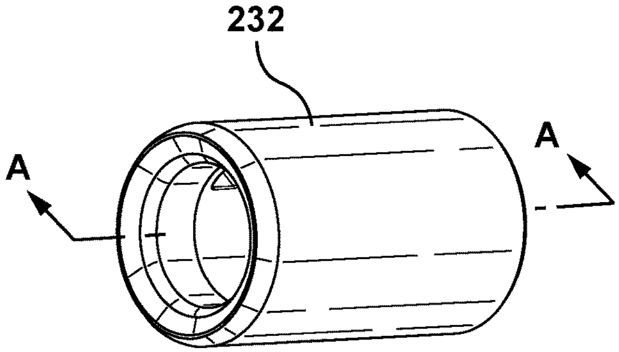
FIG. 5 depicts a perspective view of the collar of the leaflet folding accessory of FIG. 2, wherein the collar is shown removed from the leaflet folding accessory of FIG. 2 for sake of illustration only.
Figure 5A:
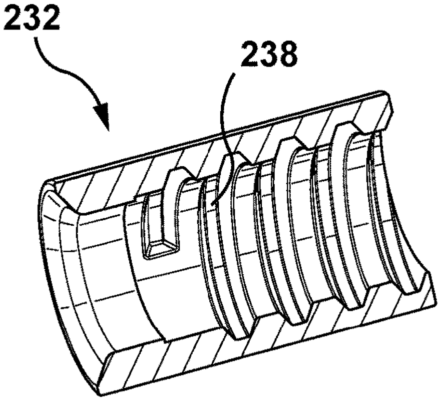
FIG. 5A is a sectional view of the collar of FIG. 5, taken along line A-A of FIG. 5.

As stated above, the main components of the leaflet folding accessory 220 include the plurality of guide fingers 222, the handle 230, and the collar 232. FIG. 3 depicts a sectional side view of the leaflet folding accessory 220, while FIG. 4 depicts a perspective view of the leaflet folding accessory 220 in which the collar 232 of the leaflet folding accessory 220 is removed for sake of illustration only. FIG. 5 depicts a perspective view of the collar 232 and FIG. 5A is a sectional view taken along line A-A of FIG. 5. In an embodiment, when the guide fingers are in the leaflet contact configuration depicted in FIGS. 2, 3, and 4, each guide finger 222 extends from the handle 230 axially and substantially parallel to a longitudinal axis of the handle 230, and axially and substantially parallel to a longitudinal axis of the transcatheter valve prosthesis 100 when in use. Each guide finger 222 includes a first end 224 that is attached to the handle 230 and a second end 226 that is spaced apart from the handle 230. The second end 226 of each guide finger 222 is unconstrained, i.e., is free or detached from any other structure. The leaflet contact portion 223 is formed closer to the second end 226 of each guide finger 222 than the first end 228. The length of the leaflet contact portion 223 depends upon the size of the transcatheter valve prosthesis 100 being crimped.

The plurality of guide fingers 222 are circumferentially spaced apart from each other. The plurality of guide fingers 222 include at least three guide fingers. As shown in the embodiment of FIGS. 2-6, the plurality of guide fingers 222 may include exactly three guide fingers 222, with each guide finger 222 being configured to contact a single leaflet 105 of the valve component 104. However, in another embodiment, the plurality of guide fingers 222 may include more than three guide fingers. The number of guide fingers 222 may depend on the number of leaflets 105 and/or the size and configuration of the frame 102. For example, the plurality of guide fingers 222 may include six guide fingers 222, with two guide fingers 222 being configured to contact a single leaflet 105 of the valve component 104. When configured for use with a valve component having single leaflet or bicuspid leaflet configuration, the number of guide fingers 222 configured to contact each leaflet may vary from the tricuspid leaflet configuration. When the leaflet accessory tool 220 includes exactly three guide fingers 222, and the transcatheter valve prosthesis 100 includes exactly three leaflets, the guide fingers 222 are circumferentially spaced apart from each other at substantially equal intervals with a single guide finger being positioned to contact a single leaflet. If the leaflet accessory tool 220 includes exactly six guide fingers 222, and the transcatheter valve prosthesis 100 includes exactly three leaflets, the guide fingers 222 are circumferentially spaced apart from each other with two guide fingers being positioned to contact a single leaflet. The two guide fingers would be positioned between commissure posts 114A of the frame 102 to form substantially equal intervals between the commissure posts 114A and each guide finger.

The handle 230 is configured to be hand-held by a user in order to position the leaflet folding accessory 220 as desired during the crimping process of the transcatheter valve prosthesis 100. The handle 230 includes a first longitudinal portion 234A and a second longitudinal portion 234B. The second longitudinal portion 234B has a smaller outer diameter than the first longitudinal portion 234A, and includes a first threaded surface 236 having a first plurality of threads formed or disposed on an outer surface thereof. The collar 232 is disposed over the second longitudinal portion 234B of the handle 230, and is configured to rotate relative thereto. More particularly, the collar 232 includes a second threaded surface 238 having a second plurality of threads formed on an inner surface thereof. The threads of the first threaded surface 236 are configured to mate with the threads of the second threaded surface 238.

The collar 232 is rotatable relative to the handle 230 in order to adjust a radial position of the leaflet contact portions 223 of the guide fingers 222. More particularly, the leaflet contact portions 223 of the guide fingers 222 may be radially compressed for easy insertion into the transcatheter valve prosthesis 100. After the guide fingers 222 are in the correct longitudinal position within the transcatheter valve prosthesis 100, the guide fingers 222 may be radially expanded to resume the leaflet contact configuration and thereby contact the leaflets 105 such that each guide finger 222 is positioned to hold at least a portion of a leaflet 105 of the transcatheter valve prosthesis 100 directly adjacent to or against an inner surface of the frame 105 of the transcatheter valve prosthesis 100. When the collar 232 is rotated in a first direction, i.e., counter clockwise or clockwise depending on the direction of the threads, the collar 232 moves in a longitudinal direction indicated by directional arrow 240 (shown on FIG. 2) towards the leaflet contact portions 223 of the guide fingers 222 due to the interaction between the mating first and second threaded surface 236, 238. As the collar 232 moves towards the leaflet contact portions 223 of the guide fingers 222, the collar 232 moves into contact with the outward bumps 242 formed on the guide fingers 222. More particularly, each guide finger 222 includes an outward bump 242 formed on a mid-portion thereof between the leaflet contact portion 223 and the first end 224. The outward bumps 242 extend radially outward relative to the remaining length of the guide finger 222, and are configured to interact with the collar 232. As the collar 232 is advanced over the outward bumps 242, the leaflet contact portions 223 of the guide fingers 222 are deflected or moved radially inward as indicated by directional arrows 244. When deflected radially inwards, the leaflet contact portions 223 may be easily positioned into the frame 102 of the transcatheter valve prosthesis 100. Once positioned as desired, a user may rotate the collar 232 in a second direction that opposes the first direction, i.e., the other of counter clockwise or clockwise, to cause the collar 232 to move back to its initial longitudinal position and permit the guide fingers 222 to resume or revert to their initial radial positions of the leaflet contact configuration.

Although the leaflet folding accessory 220 is described herein as including the collar 232, in another embodiment hereof, the collar 232 and the second longitudinal portion 234B of the handle 230 may be omitted. The guide fingers 222 may alternatively be displaced or deflected by hand (i.e., by a user) when positioning the leaflet folding accessory 220 into the transcatheter valve prosthesis 100. Further, additional configurations of the handle and collar are described in more detail herein with respect to FIGS. 23-27.

Figure 6:
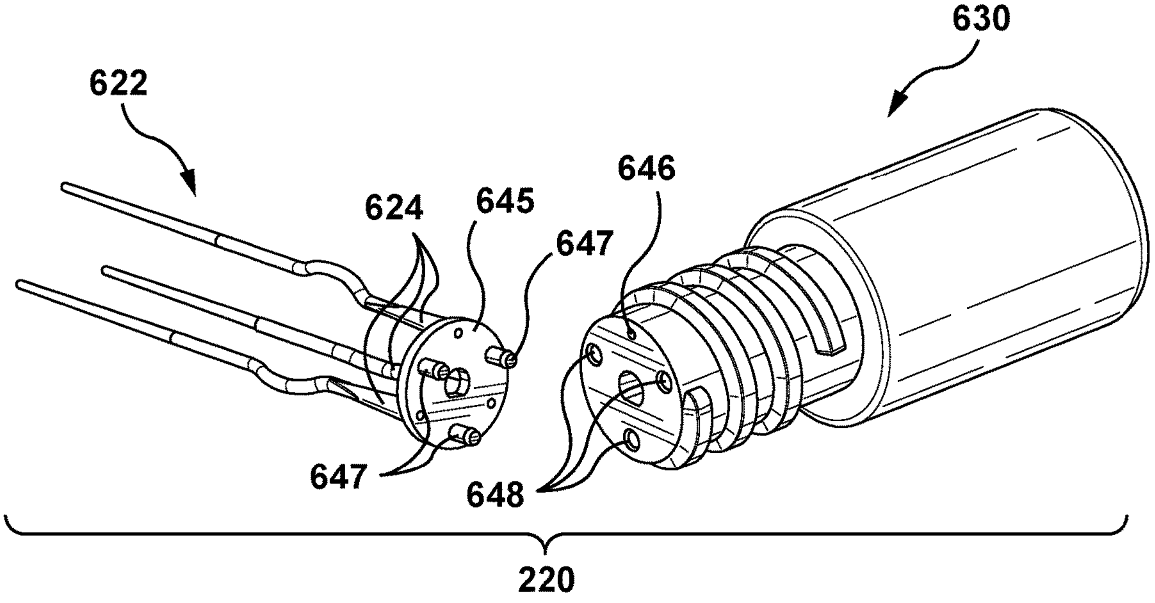
FIG. 6 depicts a perspective exploded view of a leaflet folding accessory according to another embodiment hereof, wherein guide fingers of the leaflet folding accessory are in the leaflet contact configuration and a collar of the leaflet folding accessory is removed for sake of illustration only, and wherein the guide fingers are configured to be removably coupled to a hub of the leaflet folding accessory.

In another embodiment depicted in FIG. 6, guide fingers 622 are configured to be removably coupled to a handle 630 of a leaflet folding accessory 620. More particularly, a first end 624 of each guide finger 622 is attached to a nut 645 and the nut 645 is removably attached to an end 646 of the handle 630. The nut 645 includes a plurality of protrusions 647 that are configured to be received within a plurality of holes 648 formed on the end 646 of the handle 630. The protrusions 647 are configured to be received within the holes 648, and snap-fit features may be molded on the protrusions 647 and/or the holes 648 such that the protrusions 647 are disposed within the holes 648 via a snap fit or friction fit connection. In another embodiment, the subassembly of the guide fingers 622 and the nut 645 may be attached to the handle 630 via adhesive. The size of the guide fingers 622 may vary depending on the size of the transcatheter valve prosthesis 100. Thus, the size of the guide fingers 622 on the leaflet folding accessory 620 is customizable to tailor the leaflet folding accessory 620 to the size of the transcatheter valve prosthesis 100. Manufacturability of the leaflet folding accessory 620 is improved by forming the guide fingers 622 separately from the handle 630. In addition, during assembly of the leaflet folding accessory 620, the rotatable collar 232 may be threaded onto the handle 630 prior to coupling the subassembly of the guide fingers 622 and the nut 645 to the handle 630 so that the guide fingers 622 do not undergo plastic deformation by passing the rotatable collar 232 thereover during assembly.

Figure 7:
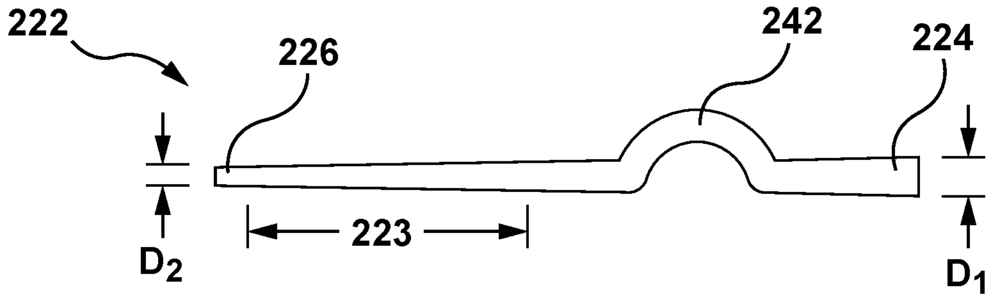
FIG. 7 is a side view of a guide finger of the leaflet folding accessory of FIG. 2, wherein the guide finger is shown removed from the leaflet folding accessory of FIG. 2 for sake of illustration only.

Turning now to FIG. 7, the contour or profile of a guide finger 222, 622 will be described in more detail. FIG. 7 is a side view of a guide finger 222 of the leaflet folding accessory 220, with the guide finger 222 being shown removed from the leaflet folding accessory 220 for sake of illustration only. The guide finger 222 is a rod having a substantially circular cross section along an entire length thereof. A diameter of the guide finger 222 tapers from the first end 224 to the second end 226 thereof. Stated another way, the first end 224 of the guide finger 222 has a first diameter $D_1$ which is greater than a second diameter $D_2$ of the second end 226 of the guide finger 222. As such, the strength of the guide finger is relatively greater at the first end 224 thereof, which is attached to the handle 630, while the flexibility of the guide finger 622 is relatively greater at the second end 226 thereof. The increased flexibility of the second end 226 permits the guide finger 622 to easily bend or flex during crimping of the transcatheter valve prosthesis 100.

As used herein, "substantially" circular cross section includes rods that have a portion thereof ovalized. In an embodiment, at least the first ends 224 of the guide fingers 222 are ovalized to inhibit circumferential displacement when the rotatable collar 232 is twisted to compress or release the guide fingers 222. By optimizing the major diameter in the circumferential direction for stability and minimizing the minor diameter in the radial direction at the first ends 224, a degree of flexure in the radial direction is enabled so that second ends 226 of the guide fingers 222 may flex inward to permit insertion to the transcatheter valve prosthesis 100 without damaging the leaflets 105. In another embodiment, the first ends 224 of the guide fingers 222 are ovalized with the major diameter in the circumferential direction and the second ends 226 of the guide fingers 222 are ovalized with the major diameter in the radial direction. By doing so the second ends 226 of the guide fingers 222 can maintain sufficient radial force while allowing void space for folding of the leaflets 105 when the transcatheter valve prosthesis 100 is crimped.

Each guide finger 222 is formed of a pliable polymer material. The polymer material of the plurality of guide fingers 222 must have sufficient stiffness to hold the leaflets 105 of the transcatheter valve prosthesis 100 in the open state when the transcatheter valve prosthesis 100 is compressed into the crimped configuration, but must also be configured to contact the leaflets 105 of the transcatheter valve prosthesis 100 without causing damage thereto. Suitable polymer materials for the plurality of guide fingers 222 include but are not limited to ePTFE, polyurethane, silicone, Acetal, Delrin, nylon, or stainless steel wire. In another embodiment, each guide finger 222 is a composite finger comprised of a metal core for stiffness and a polymer layer or coating disposed over the metal core for friction modulation. In another embodiment, each guide finger 222 is formed from a soft foam such that the guide fingers collapse while the transcatheter valve prosthesis 100 is crimped, yet still influences or guides the folding behavior of the leaflets during collapse.

Figure 7A:
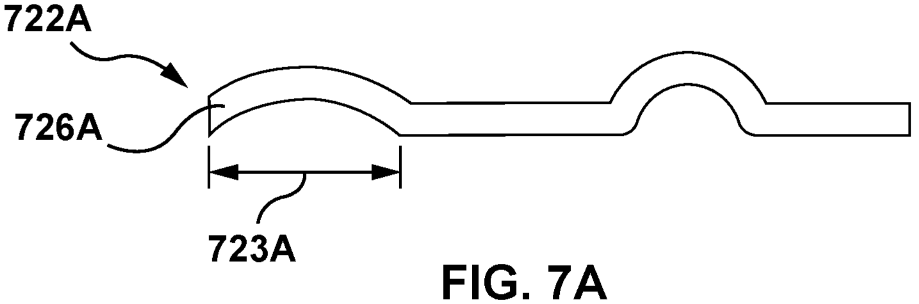
FIG. 7A is a side view of a guide finger according to another embodiment hereof, wherein the guide finger is shown removed from a leaflet folding accessory for sake of illustration only.
Figure 7B:
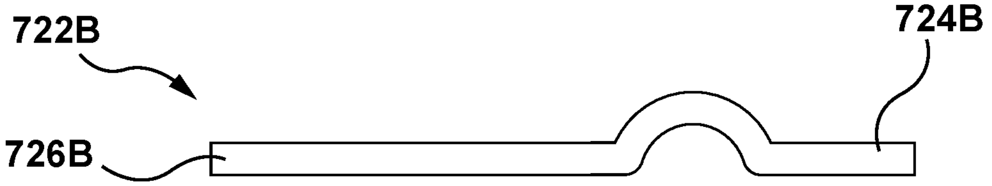
FIG. 7B is a side view of a guide finger according to another embodiment hereof, wherein the guide finger is shown removed from a leaflet folding accessory for sake of illustration only.
Figure 7C:
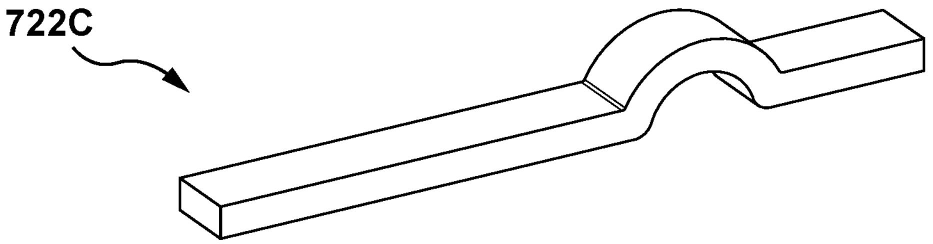
FIG. 7C is a side view of a guide finger according to another embodiment hereof, wherein the guide finger is shown removed from a leaflet folding accessory for sake of illustration only.
Figure 7D:
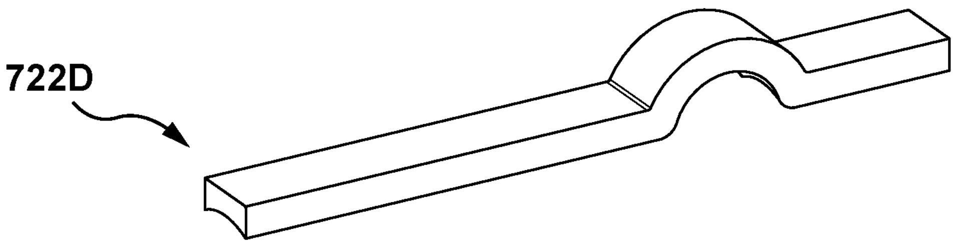
FIG. 7D is a side view of a guide finger according to another embodiment hereof, wherein the guide finger is shown removed from a leaflet folding accessory for sake of illustration only.

Although shown with a tapered profile, it will be apparent to one of ordinary skill in the art that the guide fingers 222 may have alternative profiles, contours, or geometries. FIGS. 7A-7D illustrate alternative guide finger profiles that are configured for contacting an inside surface of a leaflet 105. FIG. 7A is a side view of a guide finger 722A according to another embodiment hereof, with the guide finger 722A being shown removed from a leaflet folding accessory for sake of illustration only. The guide finger 722A includes a curved leaflet contact portion 723A adjacent to a second end 726 thereof. The curved leaflet contact portion 723A provides an atraumatic surface geometry for contacting an inside surface of a leaflet 105. FIG. 7B is a side view of a guide finger 722B according to another embodiment hereof, with the guide finger 722B being shown removed from a leaflet folding accessory for sake of illustration only. The guide finger 722B is a rod having a substantially circular cross section along an entire length thereof and a diameter of the guide finger 722B is constant from a first end 724B to a second end 726B thereof. Thus, the guide finger 722B is similar to the guide finger 222 except that the guide finger 722B does not include a taper along a length thereof. FIG. 7C is a side view of a guide finger 722C according to another embodiment hereof, with the guide finger 722C being shown removed from a leaflet folding accessory for sake of illustration only. The guide finger 722C has a flattened, ribbon-like cross section along an entire length thereof. The flattened, ribbon-like cross section of the guide finger 722D provides an atraumatic surface geometry for contacting an inside surface of a leaflet 105. FIG. 7D is a side view of a guide finger 722D according to another embodiment hereof, with the guide finger 722D being shown removed from a leaflet folding accessory for sake of illustration only. The guide finger 722D has a curved cross section along an entire length thereof. The curved cross section of the guide finger 722D provides an atraumatic surface geometry for contacting an inside surface of a leaflet 105. In addition, the curved inner surface of the guide finger 722D may be configured to mate with an outer surface of a component of the delivery system, such as the balloon of the delivery system or an outward bumper that is disposed at an end of the balloon of the delivery system.

Figure 7E:
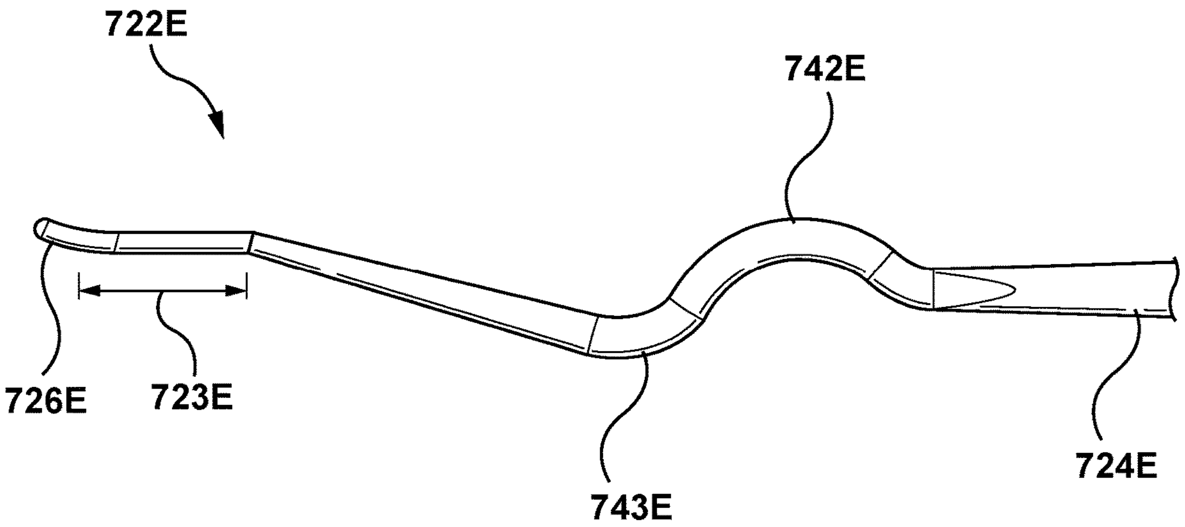
FIG. 7E is a side view of a guide finger according to another embodiment hereof, wherein the guide finger is shown removed from a leaflet folding accessory for sake of illustration only.

FIG. 7E is a side view of a guide finger 722E according to another embodiment hereof, with the guide finger 722E being shown removed from a leaflet folding accessory for sake of illustration only. Similar to the guide finger 222, the guide finger 722E is a rod having a substantially circular cross section along an entire length thereof and a diameter of the guide finger 722E tapers from the first end 724E to the second end 726E thereof. In addition, similar to the guide finger 222, each guide finger 722E includes an outward bump 742E formed on a mid-portion thereof between a leaflet contact portion 723E and the first end 724E. The outward bump 742E extend radially outward relative to the remaining length of the guide finger 722E, and are configured to interact with the collar 232. However, unlike the guide finger 222, the guide finger 722E also includes an inward bump 743E formed directly adjacent to the outward bump 742E, between the outward bump 742E and the leaflet contact portion 723E. The inward bump 743E extends in an opposing directing that the outward bump 742E, and thus extends radially inward relative to the remaining length of the guide finger 722E. Collectively, the inward bump 743E and the outward bump 742E form an S-shape or profile. The inward bump 743E functions as a stop that prohibits plastic deformation of the guide fingers 722E when they are compressed for insertion into the transcatheter valve prosthesis

100. More particularly, when radially compressed for insertion into the transcatheter valve prosthesis 100, the inward bumps 743E of the guide fingers 722E contact or abut against each other so that the guide fingers 722E cannot be over-compressed to a point in which plastic deformation of the guide fingers 722E would occur. The inward bump 743E keeps the guide fingers 722E from deflecting excessively and permanently deforming. Further, the angled straight section of the guide finger 722E between the inward bump 743E and the leaflet contact portion 723E minimizes contact with the inflow edge of the frame 102 of the transcatheter valve prosthesis 100 while maximizing contact of the second end 726E of the guide finger 722 at the edge of the leaflet 105.

Figure 8:
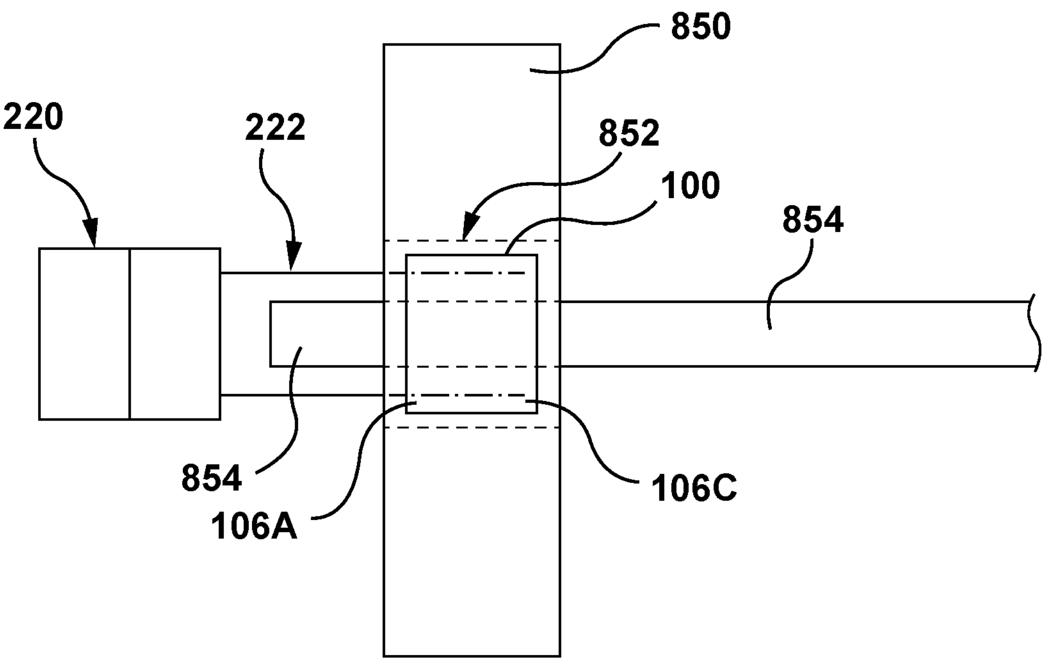
FIG. 8 depicts a schematic side view of an assembly according to embodiments thereof, the assembly including a crimper, the leaflet folding accessory of FIG. 2, and a delivery system, wherein the transcatheter valve prosthesis of FIG. 1 is disposed within a crimper chamber of the crimper and the leaflet folding accessory is disposed radially within the transcatheter valve prosthesis via an inflow end thereof.

With the structure of the leaflet folding accessory 220 described in detail above, methods of using the leaflet folding accessory 220 will now be described with references to FIGS. 8-13. FIG. 8 depicts a schematic illustration of an assembly including a crimper 850, the leaflet folding accessory 220, and a delivery system 854. In the embodiment of FIG. 8, the leaflet folding accessory 220 is disposed radially within the transcatheter valve prosthesis 100 via the inflow portion 106A thereof. An exemplary delivery system including an expandable balloon for radially expanding the transcatheter valve prosthesis 100 is described in U.S. application Ser. No. 16/907,466, filed Jun. 22, 2021, or U.S. application Ser. No. 17/406,618, filed Aug. 19, 2021, each of which is herein incorporated by reference in its entirety. However, it will be apparent to one of ordinary skill in the art that other delivery systems may be utilized and that the components of the delivery system may vary depending upon the configuration and structure of the transcatheter valve prosthesis that is being delivered. The crimper 850 may be any mechanical crimping device known in the art that is configured to radially compress the transcatheter valve prosthesis 100 from its expanded configuration to a radially compressed configuration suitable for intravascular delivery as known in the art. For example, the crimper 850 may be, for example, a crimper described in U.S. patent application Ser. No. 17/394,025, filed Aug. 4, 2021, herein incorporated by reference in its entirety.

As shown in FIG. 8, the leaflet folding accessory 220 is configured to be disposed adjacent to a distal end or tip of the delivery system 854. The transcatheter valve prosthesis 100 is disposed or positioned within a crimper chamber 852 of the crimper 850 with the inflow portion 106A thereof disposed closer to the distal end of the delivery system 854 than the outflow portion 106C thereof. As such, during crimping of the transcatheter valve prosthesis 100, the guide fingers 222 extend through the central lumen 116 of the transcatheter valve prosthesis 100 from the inflow portion 106A thereof.

Figure 9:
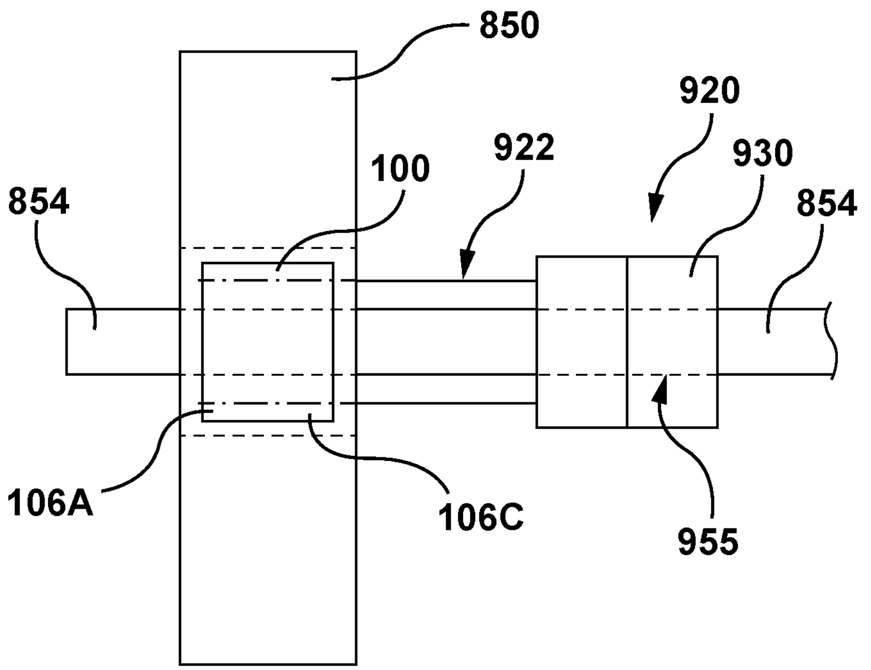
FIG. 9 depicts a schematic side view of an assembly according to embodiments thereof, the assembly including a crimper having a crimper chamber, a leaflet folding accessory according to another embodiment hereof, and a delivery system, wherein the transcatheter valve prosthesis of FIG. 1 is disposed within a crimper chamber of the crimper and the leaflet folding accessory is disposed radially within the transcatheter valve prosthesis via an outflow end thereof.

However, it will be understood by one of ordinary skill in the art that the leaflet folding accessory 220 may be modified such that it is configured to slide or otherwise be disposed over the delivery system 854. In such an embodiment, during crimping of the transcatheter valve prosthesis 100, the guide fingers may extend through the central lumen 116 of the transcatheter valve prosthesis 100 from the outflow portion 106C thereof. More particularly, FIG. 9 depicts a schematic illustration of an assembly including the crimper 850, a leaflet folding accessory 920, and the delivery system 854. The transcatheter valve prosthesis 100 is disposed or positioned within the crimper chamber 852 of the crimper 850 with the inflow portion 106A thereof disposed closer to the distal end of the delivery system 854 than the outflow portion 106C thereof, and the leaflet folding accessory 920 is disposed radially within the transcatheter valve prosthesis 100 via the outflow portion 106C thereof. The leaflet folding accessory 920 is similar to the leaflet folding accessory 220, except that a handle 930 thereof includes a lumen or passageway 955 longitudinally extending therethrough such that the leaflet folding accessory 920 may be advanced over and slide relative to an outer surface of the delivery system 854.

Figure 10:
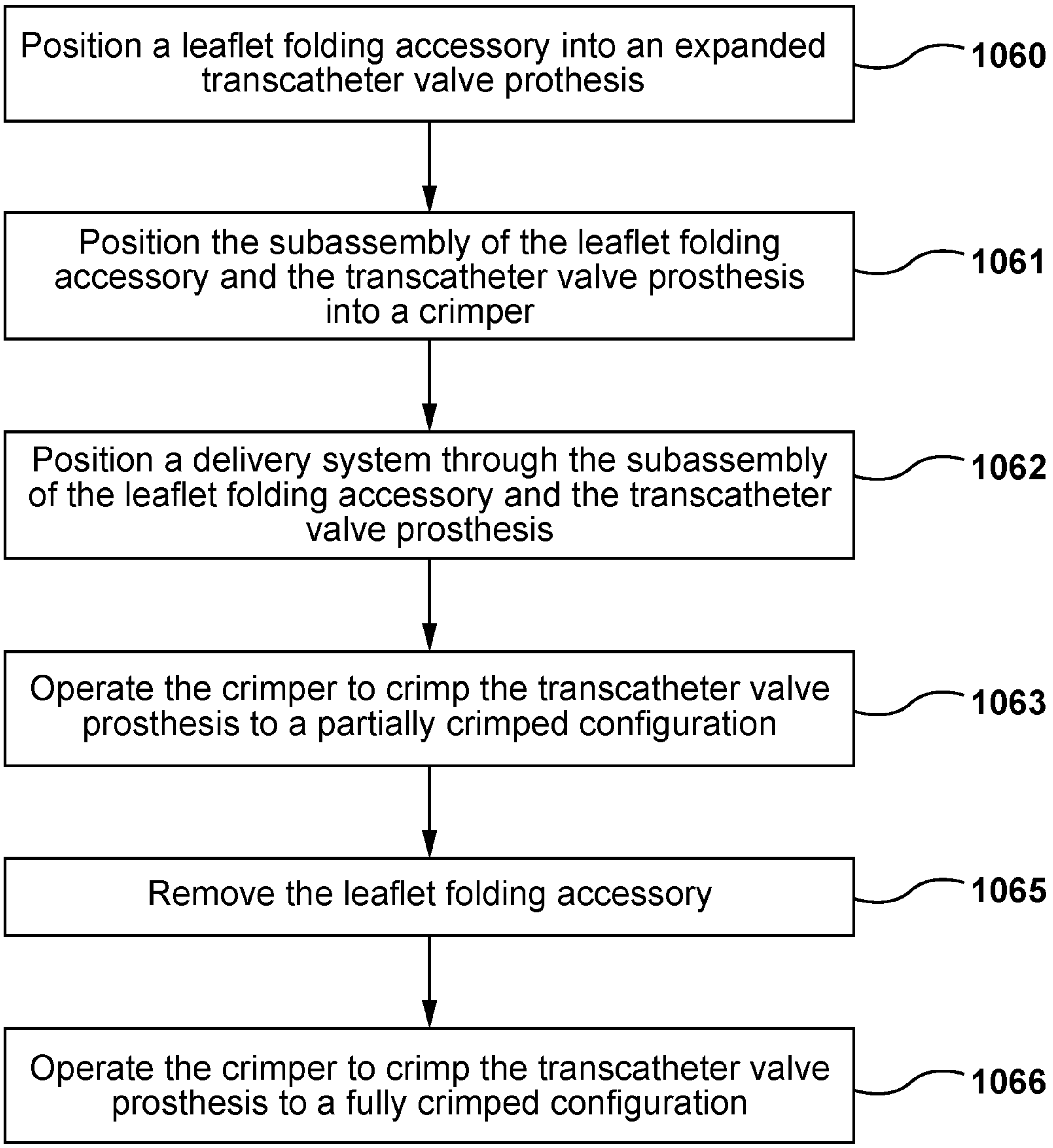
FIG. 10 depicts a method of using the leaflet folding accessory of FIG. 2 within the assembly of FIG. 8 according to an embodiment hereof.

FIG. 10 depicts method steps according to an embodiment hereof for using the leaflet folding accessory 220 during crimping of the transcatheter valve prosthesis 100 onto the delivery system 854. Although the method steps are described herein with reference to the leaflet folding accessory 220, the same method steps may be performed by the leaflet folding accessory 620, the leaflet folding accessory 920, the leaflet folding accessory 1920, or the leaflet folding accessory 2120.

With reference to step 1060 of FIG. 10, with the transcatheter valve prosthesis 100 in its expanded configuration, the leaflet folding accessory 220 is positioned through the central lumen 116 of the transcatheter valve prosthesis 100 such that the guide fingers 222 are disposed radially within the leaflets 105. In an embodiment, the step 1060 may include actuating or advancing the rotatable collar 232 of the leaflet folding accessory 220 so that the second ends 226 of the guide fingers 222 are deflected radially inwards until the contact each other. While in this radially compressed configuration, the guide fingers 222 may be inserted into the transcatheter valve prosthesis 100. In an embodiment, the guide fingers 222 are inserted into the inflow portion 106A of the transcatheter valve prosthesis 100. The plurality of guide fingers 222 of the leaflet folding accessory 220 are advanced until the leaflet contact portions 223 of the guide fingers 222 are disposed as desired longitudinally relative to the transcatheter valve prosthesis 100. In an embodiment, the plurality of guide fingers 222 of the leaflet folding accessory 220 are advanced until the leaflet contact portions 223 of the guide fingers 222 are disposed with the second ends 226 beyond or past the free edges of the leaflets 105 between 3 mm and 5 mm. The guide fingers 222 may be positioned such that each guide finger 222 is substantially aligned with a midline of a leaflet 105. A midline of a leaflet 105 is disposed equally or midway between the respective commissures of the leaflet. Aligning the guide fingers 222 with the midlines of the leaflets 105 results in the most preferential folding of the leaflets 105 because the amount of leaflet material is equally distributed around a guide finger 222. In addition, with respect to the particular structure of the transcatheter valve prosthesis 100, the midlines of the leaflets 105 are disposed adjacent to the axial struts 114B of the frame 102. Thus, when the guide fingers 222 are aligned with the midlines of the leaflets 105, each guide finger 222 is further disposed adjacent to the axial struts 114B (with material of a leaflet 105 disposed therebetween), such that the guide fingers 222 are supported during the crimping operation. The material of the leaflets 105 is essentially pinned or sandwiched between an axial strut 114B and a guide finger 222 in order to result in preferential folding of the material of the leaflets 105 between the axial struts 114B and the commissure posts 114A. The presence and location of the guide fingers 222 prevent the leaflets 105 from folding into an irregular pattern.

It will be understood by one of ordinary skill in the art that placement of the guide fingers 222 is not limited to the midlines of the leaflets 105. The placement of the guide fingers 222 depends on a number of factors including the size of the leaflets 105, the number of guide fingers of the leaflet folding accessory, and the number or placement of axial struts 114B of the frame 102.

After the guide fingers 222 are in the correct longitudinal and circumferential position within the transcatheter valve prosthesis 100, the guide fingers 7222 may be radially expanded to resume the leaflet contact configuration and thereby contact the leaflets 105 such that each guide finger 222 is positioned to hold at least a portion of a leaflet 105 of the transcatheter valve prosthesis 100 directly adjacent to or against an inner surface of the frame 105 of the transcatheter valve prosthesis 100. More particularly, the collar 232 is rotated or otherwise caused to move back to its initial longitudinal position and permit the guide fingers 222 to resume or revert to their initial radial positions of the leaflet contact configuration. In an embodiment, once in the leaflet contact configuration, the second ends 226 of the guide fingers 222 extend uniformly between 3 mm and 5 mm beyond or past the free edges of the leaflets 105.

With reference to step 1061 of FIG. 10, the subassembly of the leaflet folding accessory 220 and the transcatheter valve prosthesis 100 is positioned into the crimper chamber 852 of the crimper 850. It will be understood by one of ordinary skill in the art that the subassembly of the leaflet folding accessory 220 and the transcatheter valve prosthesis 100 may be advanced into the crimper chamber 852 or the crimper 850 may be positioned around the transcatheter valve prosthesis 100 such that the crimper 850 circumferentially surrounds the transcatheter valve prosthesis 100.

Figure 11:
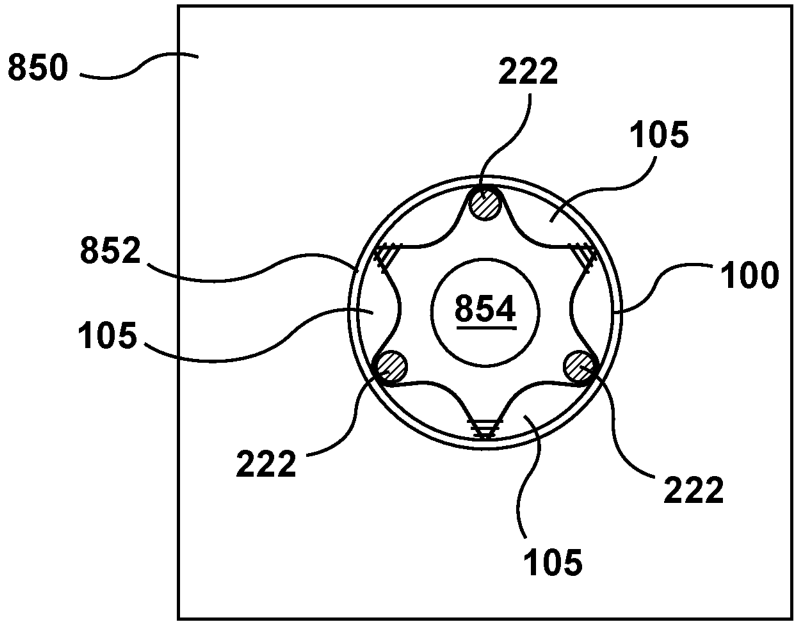
FIG. 11 depicts an end view of the crimper chamber of FIG. 8, wherein the transcatheter valve prosthesis is in a radially expanded configuration.

With reference to step 1062 of FIG. 10, as well as FIG. 11, the delivery system 854 is positioned through the subassembly of the transcatheter valve prosthesis 100 and the leaflet folding accessory 220. The delivery system 854 is advanced through the crimper 850 until the balloon of the delivery system 854 is disposed as desired longitudinally relative to the transcatheter valve prosthesis 100. FIG. 11 depicts an end view of the crimper chamber 852, with the subassembly of the transcatheter valve prosthesis 100 and the leaflet folding accessory 220 disposed therein, and the delivery system 854 disposed therethrough. The transcatheter valve prosthesis 100 is in a radially expanded configuration, and each guide fingers 222 is substantially aligned with a midline of a leaflet 105 as described above.

Figure 12:
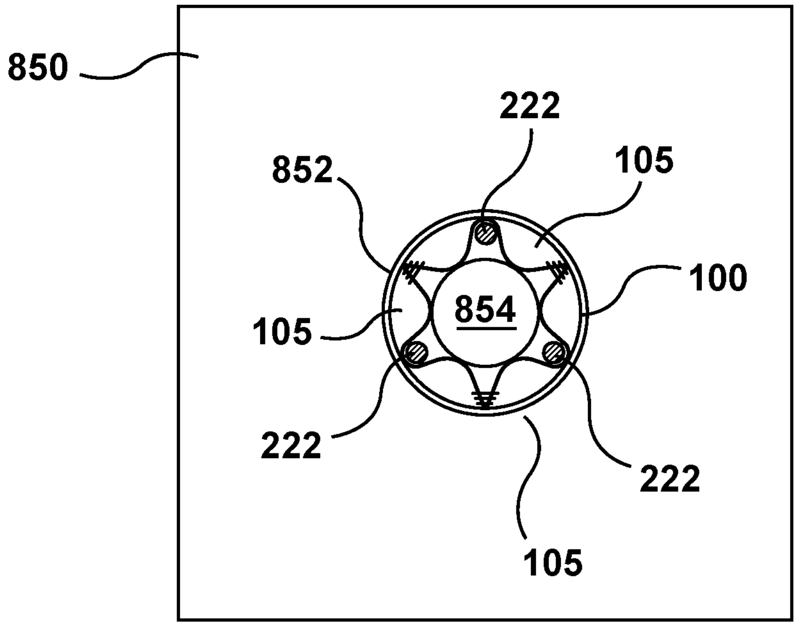
FIG. 12 depicts an end view of the crimper chamber of FIG. 8, wherein the transcatheter valve prosthesis is in a partially crimped configuration.

With reference to step 1063 of FIG. 10, as well as FIG. 12, the crimper 850 is operated to radially compress the transcatheter valve prosthesis 100 to a partially crimped configuration onto the balloon of the delivery system 854. During operation of the crimper 850, the leaflet folding accessory 220 remains positioned or disposed radially within the leaflets 105 of the transcatheter valve prosthesis 100, with the leaflet contact portion 223 of each guide finger 220 contacting and holding the leaflets 105 of the transcatheter valve prosthesis 100 against the axial struts 114B of the frame 102. As described above, by pinning or sandwiching the material of the leaflets between an axial strut 114B and a guide finger 222, the leaflets 105 fold into a predetermined pattern during crimping of the transcatheter valve prosthesis 100 which prevents any leaflet damage and/or irregular folding patterns that adversely affect the delivery profile of the transcatheter valve prosthesis 100. When all the leaflets 105 are held in a defined pattern via the plurality of guide fingers 222, each leaflet 105 folds at a consistent rate and in a consistent pattern with each other leaflet 105, thereby allowing more packing of the leaflet material without damaging any leaflet. This preferentially folded pattern of the leaflets 105 result in a smaller delivery profile or diameter of the transcatheter valve prosthesis 100 in the crimped configuration, and further the predetermined folded pattern includes a controlled distribution of stresses and strains in the leaflets 105 which minimizes the risk of leaflet damage.

FIG. 12 depicts an end view of the crimper chamber 852, with the subassembly of the transcatheter valve prosthesis 100 and the leaflet folding accessory 220 disposed therein, and the delivery system 854 disposed therethrough. The transcatheter valve prosthesis 100 is in a partially crimped configuration. Each guide finger 222 is substantially aligned with a midline of a leaflet 105, and the material of the leaflets 105 extending between the axial struts 114B and the commissure posts 114A is folded in a radially inward direction. The material of the leaflets 105 that is folded in a radially inward direction may be considered an infold, and the material of the leaflets 105 disposed between the guide fingers 222 and the frame 102 may be considered an outfold such that the folded pattern includes alternating folds or pleats (i.e., infolds and outfolds).

The crimper 850 is configured to radially compress the transcatheter valve prosthesis 100 into a crimped configuration suitable for delivery within a vasculature. As used herein, "partially crimped" includes configurations radially compressed up to 90% of the crimped configuration suitable for delivery within a vasculature, which may also be referred to herein as a fully crimped configuration. As the crimping process nears completion and the transcatheter valve prosthesis 100 nears its fully crimped configuration, the leaflets 105 have preferentially folded as described above and therefore, the leaflet folding accessory 200 may be removed prior to completing the crimping process. Removal of the leaflet folding accessory 200 allows the transcatheter valve prosthesis 100 to be radially compressed to a smaller diameter, since the guide fingers 222 are no longer disposed radially within the transcatheter valve prosthesis.

Figure 14:
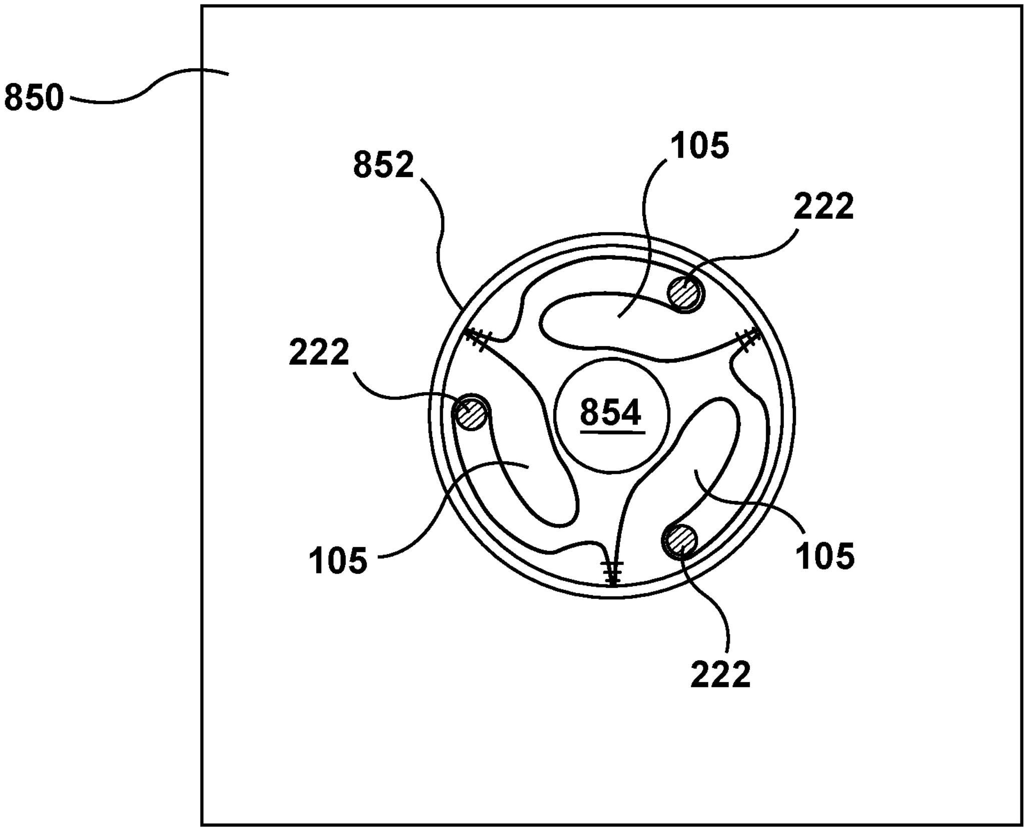
FIG. 14 depicts an end view of the crimper chamber of FIG. 8, wherein the transcatheter valve prosthesis is in a partially crimped configuration after the step of twisting of leaflet folding accessory of the method of FIG. 13.

With reference to step 1065 of FIG. 10, after the crimper 850 is operated to partially crimp the leaflet folding accessory 220 with the leaflets 105 preferentially folded as described above, the leaflet folding accessory 220 is withdrawn and removed from within the transcatheter valve prosthesis 100. At this stage of the method, the crimper 850 is still positioned over the radially compressed transcatheter valve prosthesis 100 as shown in FIG. 14. After removal of the leaflet folding accessory 220, the leaflets 105 remain folded in the predetermined pattern within the partially crimped transcatheter valve prosthesis 100.

With reference to step 1066 of FIG. 10, after removal of the leaflet folding accessory 220, the crimper 850 is operated to further crimp or radially compress the transcatheter valve prosthesis 100 to its fully crimped configuration, which is suitable for delivery within a vasculature. When the transcatheter valve prosthesis 100 is fully crimped, the leaflets 105 remain folded in the predetermined pattern therein. With the transcatheter valve prosthesis 100 crimped onto the balloon of the delivery system 854, the crimper 850 may be removed.

Figure 13:
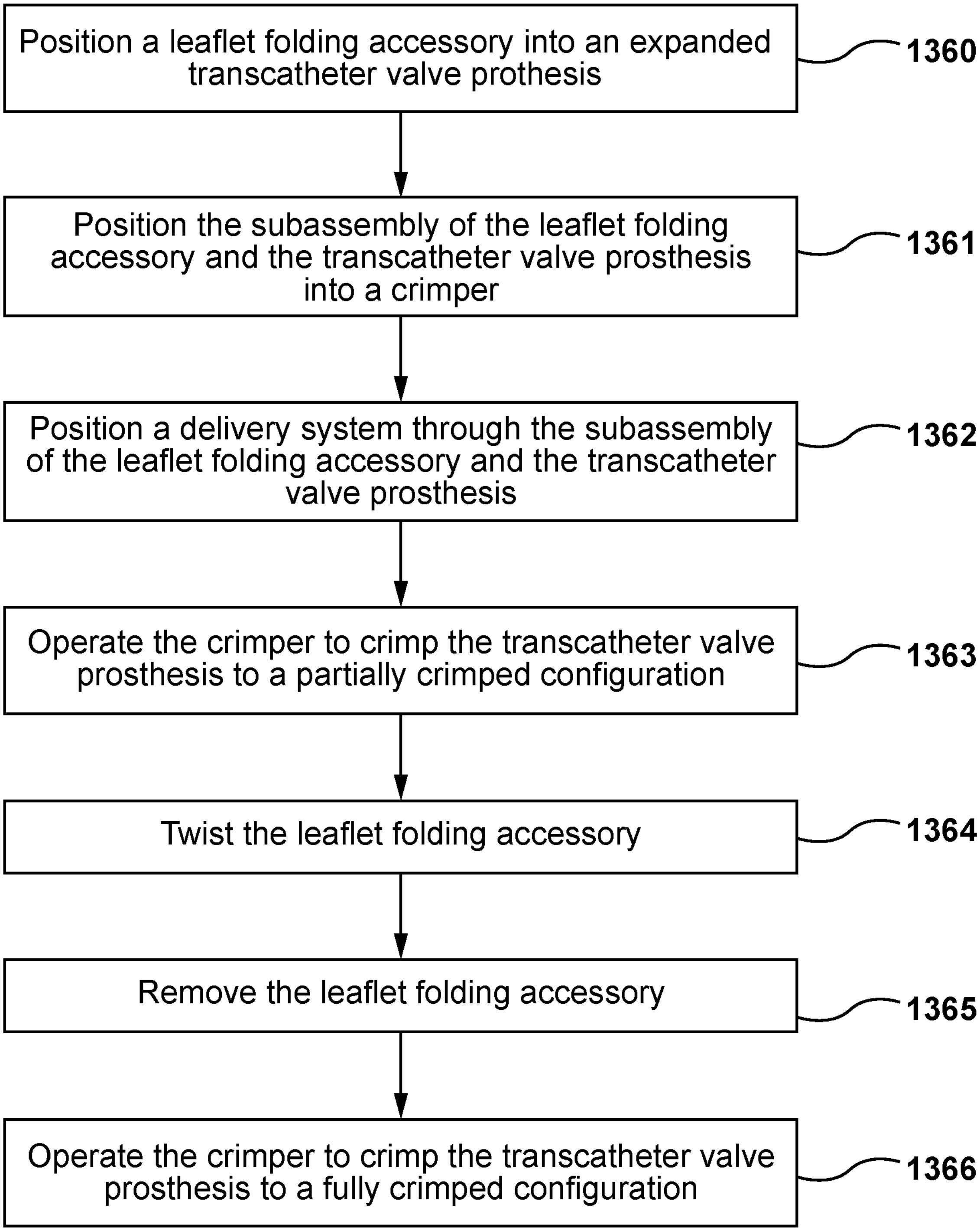
FIG. 13 depicts a method of using the leaflet folding accessory of FIG. 2 within the assembly of FIG. 8 according to another embodiment hereof.

FIG. 13 depicts another method of using the leaflet folding accessory 220 within the assembly of FIG. 8. Although the method steps are described herein with reference to the leaflet folding accessory 220, the same method steps may be performed by the leaflet folding accessory 620, the leaflet folding accessory 920, or the leaflet folding accessory 2120. Steps 1360, 1361, 1362, 1363, 1365, and 1366 of this method are the same as steps 1160, 1161, 1162, 1163, 1165, and 1166 of the method described in relation to FIG. 11. However, in this embodiment, an additional method step 1364 is included between the step 1363 and step 1365.

In step 1363, the crimper 850 is operated to radially compress the transcatheter valve prosthesis 100 to a partially crimped configuration onto the balloon of the delivery system 854. During or after step 1363, the leaflet folding accessory 222 may be twisted as shown in step 1364. Twisting of the leaflet folding accessory 222 causes the guide fingers 222 to move in circumferential direction relative to the frame 102. The guide fingers 222 move circumferentially until they abut against a commissure post 114A of the frame 102. The material of the leaflet 105 is disposed or folded around the guide finger 222, and movement of the guide finger 222 also moves or displaces the leaflet folds therewith. Thus, the step of twisting the leaflet folding accessory 220 pulls the folded leaflet material circumferentially and results in a spiral folded pattern as shown in FIG. 14. FIG. 14 depicts an end view of the crimper chamber 852, with the subassembly of the transcatheter valve prosthesis 100 and the leaflet folding accessory 220 disposed therein, and the delivery system 854 disposed therethrough. The transcatheter valve prosthesis 100 is in a partially crimped configuration after the step 1363 of twisting of leaflet folding accessory 220, and the leaflets 105 are disposed radially inwards of the frame 102 in a spiral folded pattern.

Although the methods of use described above with respect to FIG. 10 and FIG. 13 include removal of the leaflet folding accessory 220 after partial crimping of the transcatheter valve prosthesis 100, in another embodiment hereof, the leaflet folding accessory 220 may remain disposed within the transcatheter valve prosthesis 100 for the entire crimping procedure. Stated another way, after removal of the leaflet folding accessory 220, further crimping of the transcatheter valve prosthesis 100 is not necessarily required. The necessity for further crimping after removal of the leaflet folding accessory 220 depends upon the size of the transcatheter valve prosthesis 100 and/or the final desired crossing profile of the transcatheter valve prosthesis 100.

Figure 15:
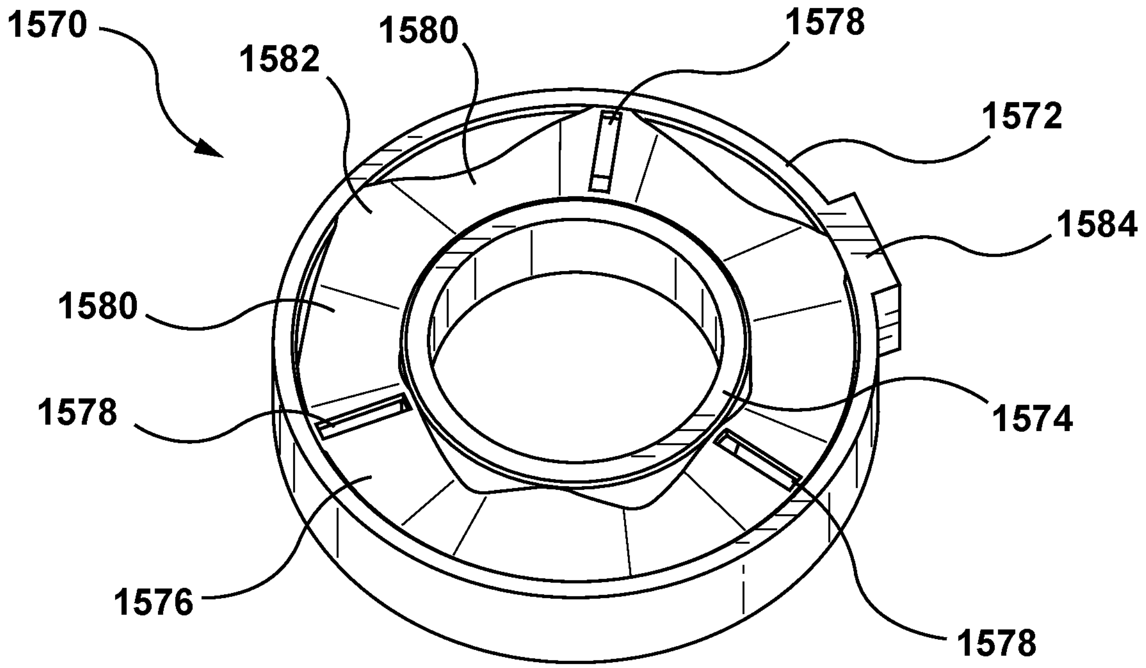
FIG. 15 depicts a perspective view of a valve seat locator according to an embodiment hereof, wherein the valve seat locator is configured to be used when positioning the leaflet folding accessory of FIG. 2 within the transcatheter valve prosthesis of FIG. 1.
Figure 16:
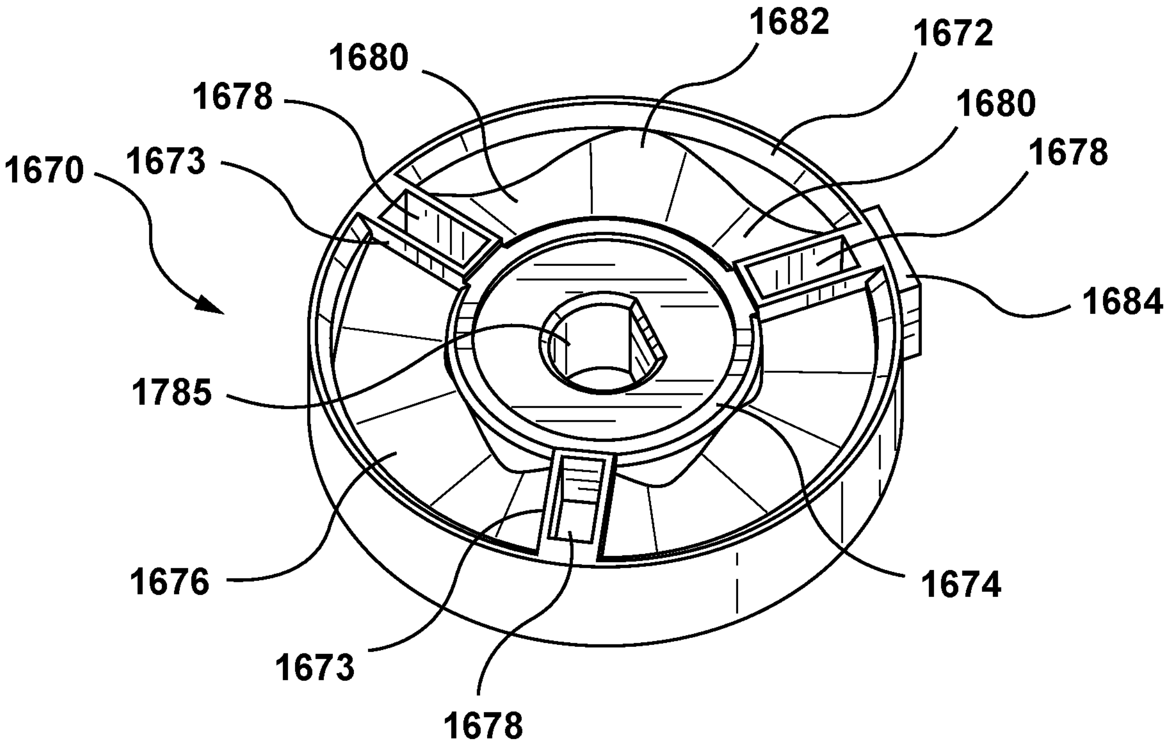
FIG. 16 depicts a perspective view of a valve seat locator according to another embodiment hereof, wherein the valve seat locator is configured to be used when positioning the leaflet folding accessory of FIG. 2 within the transcatheter valve prosthesis of FIG. 1.
Figure 17:
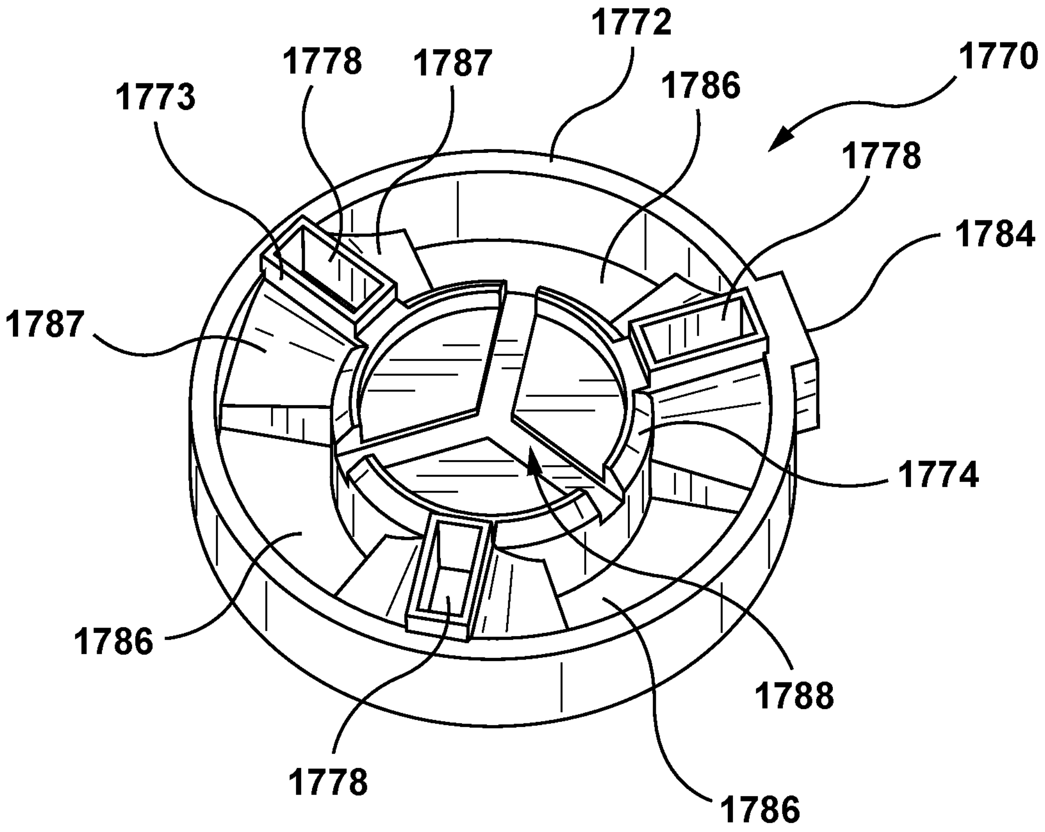
FIG. 17 depicts a perspective view of a valve seat locator according to another embodiment hereof, wherein the valve seat locator is configured to be used when positioning the leaflet folding accessory of FIG. 2 within the transcatheter valve prosthesis of FIG. 1.

It may be desirable to utilize a valve seat locator when performing steps 1160, 1360 of FIGS. 11, 13, respectively. More particularly, as previously described with respect to step 1160, it is advantageous to position the leaflet folding accessory 220 within the transcatheter valve prosthesis 100 such that each guide finger 222 is substantially aligned with a midline of a leaflet 105. Aligning the guide fingers 222 with the midlines of the leaflets 105 result in the most preferential folding of the leaflets because the amount of leaflet material is equally distributed around a guide finger 222, and because the midlines of the leaflets 105 are disposed adjacent to the axial struts 114B of the frame 102. FIGS. 15-17 depict embodiments of a valve seat locator or tool that can be utilized to align the guide fingers 222 with the midlines of the leaflets 105.

More particularly, FIG. 15 depicts a perspective view of a valve seat locator 1570 that is configured to be used when positioning the leaflet folding accessory 220 within the transcatheter valve prosthesis 100. The valve seat locator 1570 includes an outer annular member or ring 1572, an inner annular member or ring 1574 disposed radially within the outer ring 1572, and a planar component 1576 disposed between the outer and inner rings 1572, 1574. The planar component 1576 is undulating or wavy and includes a plurality of peaks 1582 and a plurality of valleys 1580, with each valley 1582 formed between a pair of adjacent peaks 1582. The frame 102 of the transcatheter valve prosthesis 100 is positioned onto the valve seat locator 1570 such that the crowns 110C of the outflow portion 106C of the transcatheter valve prosthesis 100 sit or are received within the valleys 1580. Three of the peaks 1582 of the valve seat locator 1570 may include a slot 1578. Although not shown on the embodiment of FIG. 1, the commissure posts 114A may be extended towards the crowns 110C and configured to be received within the slots 1578. The valve seat locator 1570 further includes a protrusion 1584 formed on the outer ring 1572. The handle 230 of the leaflet folding accessory 220 may include a protrusion thereon that is the same as or similar to the protrusion 1584, so that the user can circumferentially align the protrusion on the handle 230 with the protrusion 1584 when positioning the leaflet folding accessory 220 relative to the transcatheter valve prosthesis. These features ensure that the transcatheter valve prosthesis 100 and the leaflet folding accessory 220 are oriented such that each guide finger 222 is substantially aligned with a midline of a leaflet 105 when the leaflet folding accessory 220 is positioned into the transcatheter valve prosthesis 100. The valve seat locator 1570 ensures alignment of the leaflet folding accessory 220 and the transcatheter valve prosthesis 100, because the commissure posts 114A are inserted into the slots 1578 of the valve seat locator 1570 and the handle 230 may be aligned parallel with the protrusion 1584 formed on the outer ring 1572, thereby ensuring that the second ends 226 of the guide fingers 222 align as desired with the midlines of the leaflets 105.

FIG. 16 depicts a perspective view of another embodiment of a valve seat locator 1670 that is configured to be used when positioning the leaflet folding accessory 220 within the transcatheter valve prosthesis 100. The valve seat locator 1670 includes an outer annular member or ring 1672, an inner annular member or ring 1674 disposed radially within the outer ring 1672, a plurality of bosses 1673 extending between the outer and inner rings 1672, 1674, and a plurality of planar components 1676 extending between adjacent pairs of bosses 1673. Each boss 1673 defines a slot 1678. Although not shown on the embodiment of FIG. 1, the commissure posts 114A may be extended towards the crowns 110C and configured to be received within the slots 1678. Each planar component 1676 is undulating or wavy and includes a peak 1682 and a pair of valleys 1680, with the peak 1682 formed between the pair of valleys 1680. The frame 102 of the transcatheter valve prosthesis 100 is positioned onto the valve seat locator 1670 such that the crowns 110C of the outflow portion 106C of the transcatheter valve prosthesis 100 sit or are received within the valleys 1680. The curvature of the planar component 1676 is configured such that the height of the peaks 1682 do not interfere with the resting position of the leaflets 105. The valve seat locator 1670 further includes a protrusion 1684 formed on the outer ring 1672. The handle 230 of the leaflet folding accessory 220 may include a protrusion thereon that is the same as or similar to the protrusion 1684, so that the user can circumferentially align the protrusion on the handle 230 with the protrusion 1684 when positioning the leaflet folding accessory 220 relative to the transcatheter valve prosthesis. Further, the valve seat locator 1670 includes a D-shaped opening 1785 formed within the inner ring 1674. The handle 230 of the leaflet folding accessory 220 may include a D-shaped opening thereon that is the same as or similar to the D-shaped opening 1785, and a D-shaped post (not shown) may be inserted or disposed within the both of the D-shaped openings of the valve seat locator 1670 and the handle 230 to ensure correct alignment when positioning the leaflet folding accessory 220 relative to the transcatheter valve prosthesis 100. The D-shaped openings 1785, as well as the mating protrusions 1684, ensure that the transcatheter valve prosthesis 100 and the leaflet folding accessory 220 are oriented such that each guide finger 222 is substantially aligned with a midline of a leaflet 105 when the leaflet folding accessory 220 is positioned into the transcatheter valve prosthesis 100. Although the opening 1785 is described above as D-shaped, the shape thereof is not critical and any shape or configuration may be used that provides interlocking between the opening and a post inserted therein.

FIG. 17 depicts a perspective view of another embodiment of a valve seat locator 1770 that is configured to be used when positioning the leaflet folding accessory 220 within the transcatheter valve prosthesis 100. The valve seat locator 1770 includes an outer annular member or ring 1772, an inner annular member or ring 1774 disposed radially within the outer ring 1772, a plurality of bosses 1773 extending between the outer and inner rings 1772, 1774, and a pair of ramps 1787 extending from opposing sides of each boss 1773. Each boss 1773 defines a slot 1778. Although not shown on the embodiment of FIG. 1, the commissure posts 114A may be extended towards the crowns 110C and configured to be received within the slots 1778. Each ramp 1787 extends in a circumferential direction from a boss 1773, and gaps or openings 1786 are formed between adjacent ramps 1787 of adjacent bosses 1773. Openings 1786 allow for the drainage of liquid as the transcatheter valve prosthesis 100 is positioned into the valve seat locator 1770. The frame 102 of the transcatheter valve prosthesis 100 is positioned onto the valve seat locator 1770 such that the commissure posts 114A are received within or at least adjacent to the slots 1778. The ramps 1787 support the outflow portion 110C of the transcatheter valve prosthesis 100. The valve seat locator 1770 further includes a protrusion 1784 formed on the outer ring 1772. The handle 230 of the leaflet folding accessory 220 may include a protrusion thereon that is the same as or similar to the protrusion 1784, so that the user can circumferentially align the protrusion on the handle 230 with the protrusion 1784 when positioning the leaflet folding accessory 220 relative to the transcatheter valve prosthesis. Further, the valve seat locator 1670 includes a plurality of channels or grooves 1786 formed within the inner ring 1674. The grooves 1786 are configured to receive the second ends 226 of the guide fingers 222 therein to ensure correct alignment when positioning the leaflet folding accessory 220 relative to the transcatheter valve prosthesis 100. The grooves 1786, as well as the mating protrusions 1784, ensure that the transcatheter valve prosthesis 100 and the leaflet folding accessory 220 are oriented such that each guide finger 222 is substantially aligned with a midline of a leaflet 105 when the leaflet folding accessory 220 is positioned into the transcatheter valve prosthesis 100.

Figure 18:
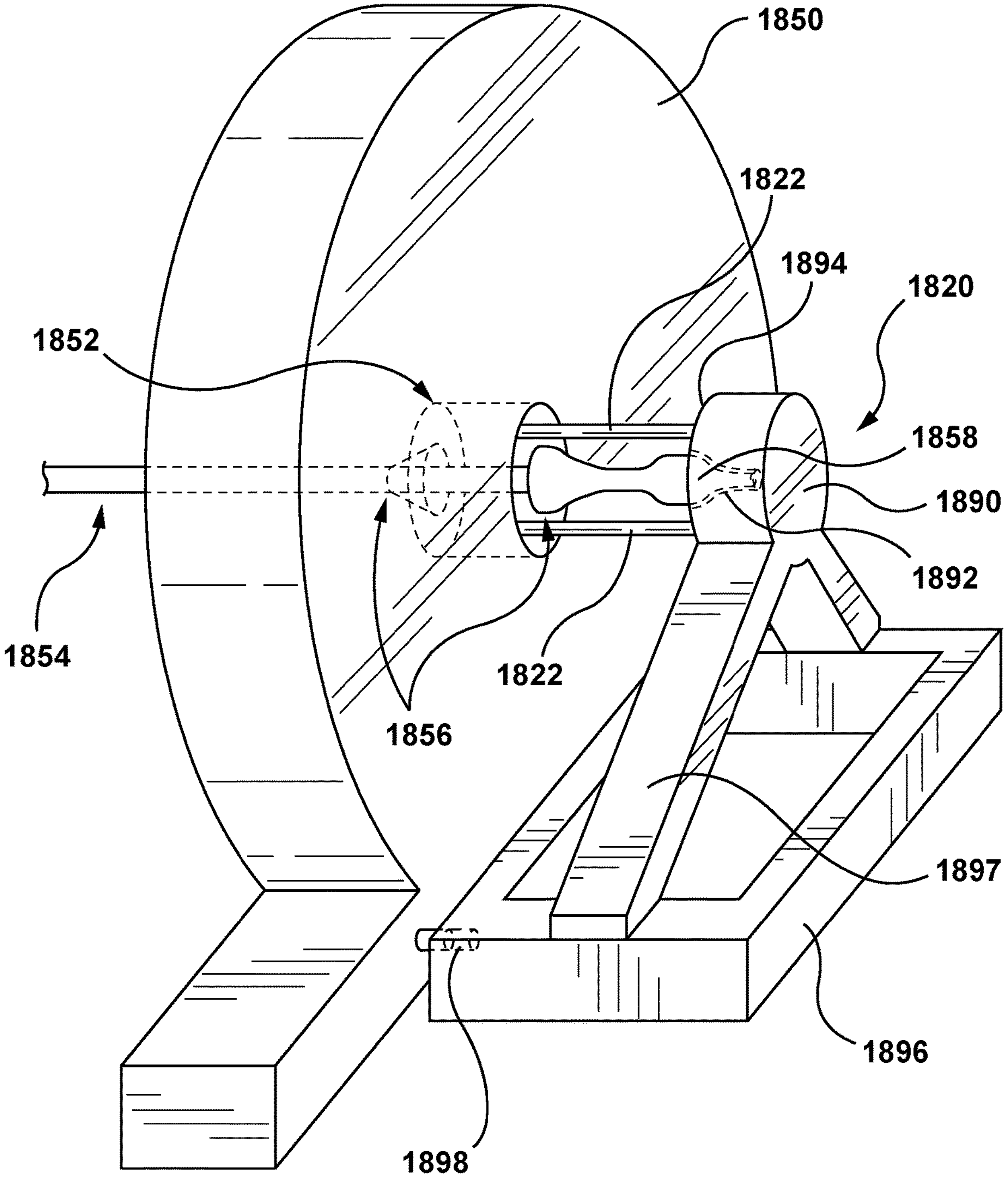
FIG. 18 depicts a schematic perspective view of an assembly according to another embodiment thereof, the assembly including a crimper having a crimper chamber, a leaflet folding accessory according to another embodiment hereof, and a delivery system, wherein the leaflet folding accessory is also configured to receive a distal end of the delivery system to provide longitudinal and circumferential centering of the delivery system within the crimper chamber.

Although the embodiments described above illustrate a hand-held leaflet folding accessory, guide fingers may be a component of a fixture that is utilized with a crimper. For example, in the embodiment of FIG. 18, a leaflet folding accessory 1820 having a plurality of guide fingers 1822 is a fixture. FIG. 18 depicts a schematic perspective view of an assembly including a crimper 1850 having a crimper chamber 1852, the leaflet folding accessory 1822, and a delivery system 1854. In this embodiment, in addition to including guide fingers 1822 for providing preferential folding of leaflets of a transcatheter valve prosthesis, the leaflet folding accessory 1820 is also configured to receive a distal end 1858 of the delivery system 1854 to provide longitudinal and circumferential centering of the delivery system 1854 within the crimper chamber 1852. An exemplary delivery system including an expandable balloon for radially expanding the transcatheter valve prosthesis is described in U.S. application Ser. No. 16/907,466, filed Jun. 22, 2021, or U.S. application Ser. No. 17/406,618, filed Aug. 19, 2021, previously incorporated by reference. However, it will be apparent to one of ordinary skill in the art that other delivery systems may be utilized and that the components of the delivery system may vary depending upon the configuration and structure of the transcatheter valve prosthesis that is being delivered. The crimper 1850 may be any mechanical crimping device known in the art that is configured to radially compress a transcatheter valve prosthesis from its expanded configuration to a radially compressed configuration suitable for intravascular delivery as known in the art. For example, the crimper 1850 may be, for example, a crimper described in U.S. patent application Ser. No. 17/394,025, filed Aug. 4, 2021, herein incorporated by reference in its entirety.

The leaflet folding accessory 1820 includes a base 1896 that is configured to be placed on a flat surface (i.e., a table top or a floor). The base 1896 is configured to be attached to the crimper 1850 via one or more pins 1898. The leaflet folding accessory 1820 also includes a hub 1890 that is attached to the base 1896 via an arm 1897. The height or placement of the arm 1897 may be fixed in order to position the hub 1890 to be longitudinally and circumferentially aligned with the crimper chamber 1852 of the crimper 1850. In another embodiment (not shown), the height or placement of the arm 1897 may be adjustable. The hub 1890 includes a recess 1892 formed on an outer surface 1894 thereof. The recess 1892 has a size and shape so as to be configured to receive the distal end 1858 of the delivery system 1854. The size and shape of the recess 1892 may mate with the distal end 1858 of the delivery system 1854 such that undesired movement of the distal end 1858 is not permitted when the distal end 1858 is positioned into the recess 1892. The hub 1890 functions as a stop for the distal tip 1858 of the delivery system 1854 and is longitudinally spaced apart from the crimper chamber 1852 at a predetermined distance that results in longitudinally centering of the delivery system 1854 within the crimper chamber 1852. Particularly, the delivery system 1854 is positioned such that the transcatheter valve prosthesis is longitudinally centered between the pair of outward bumpers 1856 of the delivery system 1854. The outward bumpers 1856 are described in more detail in U.S. application Ser. No. 17/406,618, filed Aug. 19, 2021, previously incorporated by reference. In addition, the hub 1890 is circumferentially aligned with the crimper chamber 1852 so that the delivery system 1854 is circumferentially aligned within the crimper chamber 1852 as well.

The plurality of guide fingers 1822 extend from the outer surface 1894 of the hub 1890, towards the crimper chamber 1852. In an embodiment, the guide fingers 1822 have a curved cross section along an entire length thereof as shown on guide finger 722D described above. The curved cross section is configured to mate with an outer surface of profile of an outward bumper 1856 on the delivery system 1854. In FIG. 18, the guide fingers 1822 are depicted in a leaflet contact configuration in which a leaflet contact portion of each guide finger 1822 is disposed within the crimper chamber 1852 such that the guide fingers 1822 would be disposed radially within the frame 102 of the transcatheter valve prosthesis 100 and contact an inner surface of the leaflets 105. In the same manner as described above with respect to the guide fingers 222, during crimping of the transcatheter valve prosthesis 100, the plurality of guide fingers 1822 remain disposed radially within the frame 102 such that the leaflets 105 of the valve component 104 preferentially fold around the plurality of guide fingers 1822. The guide fingers 1822 are configured to contact only the inner surfaces of the leaflets 105 of the valve component 104. Stated another way, all of the guide fingers 1822 are radially disposed entirely within the leaflets 105 of the valve component 104 and are configured such that the guide fingers 1822 do not directly contact the outer surface of the leaflets 105 and do not directly contact the frame 102 of the transcatheter valve prosthesis 100.

Figure 19:
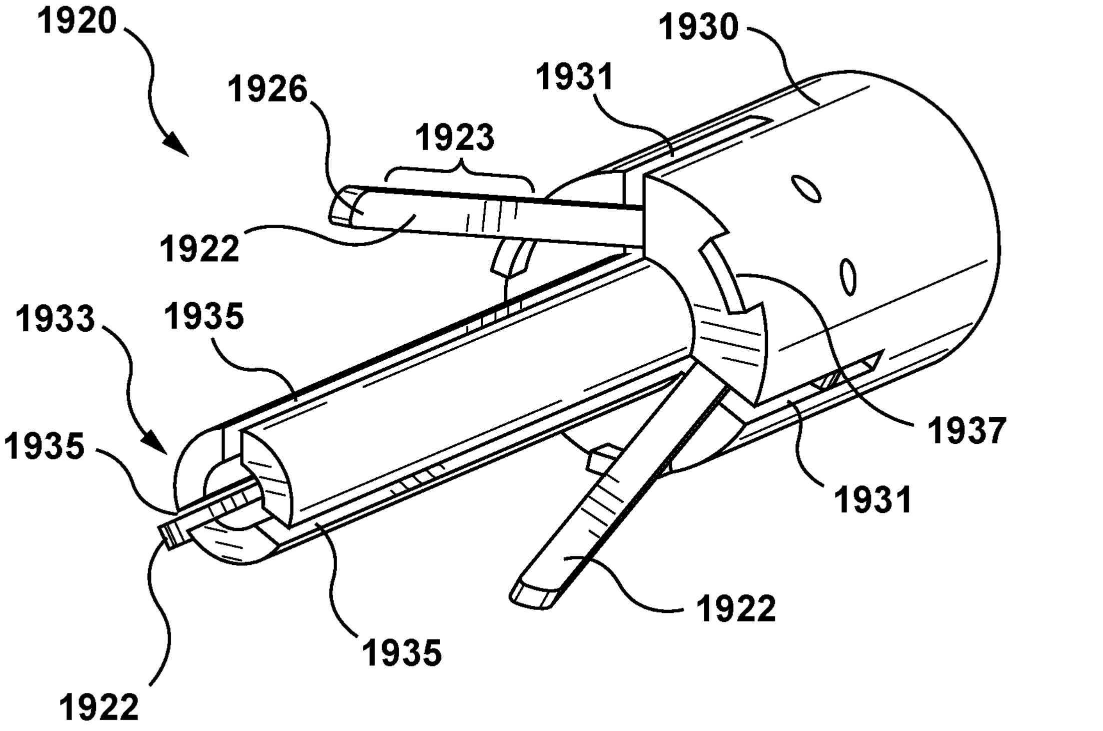
FIG. 19 depicts a perspective view of a leaflet folding accessory in accordance with another aspect of the disclosure, wherein guide fingers of the leaflet folding accessory are in a leaflet contact configuration and a hub of the leaflet folding accessory includes a plurality of slots for controlled movement of the guide fingers during use of the leaflet folding accessory.
Figure 20:
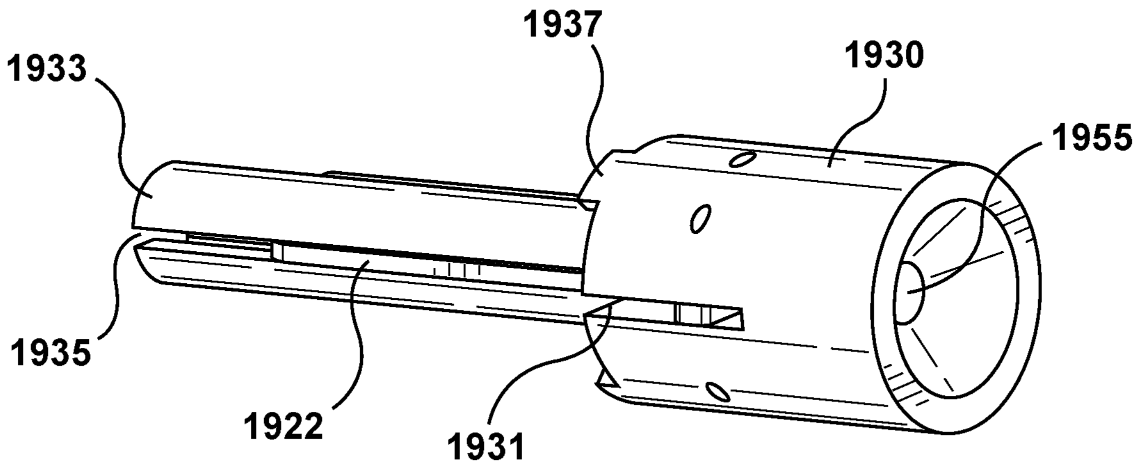
FIG. 20 depicts a perspective view of the leaflet folding accessory of FIG. 19, wherein the guide fingers of the leaflet folding accessory are radially collapsed.

FIGS. 19 and 20 illustrate another example of a leaflet folding accessory 1920 that is configured to attach to a crimper (not shown in FIGS. 19-20) during use thereof. The leaflet folding accessory 1920 is thus a removable accessory that may be attached and detached to the crimper as desired by the user. FIG. 19 depicts a perspective view of the leaflet folding accessory 1920 with guide fingers 1922 thereof in a leaflet contact configuration while FIG. 20 depicts a perspective view of the leaflet folding accessory 1920 with the guide fingers 1922 is a radially collapsed configuration. In this embodiment, as will be explained in more detail herein, a hub 1930 of the leaflet folding accessory 1920 is configured to attach to a crimper during use and further the hub 1930 includes a plurality of slots 1931 for controlled radial movement of the guide fingers 1922 during use of the leaflet folding accessory 1920.

The leaflet folding accessory 1920 includes a plurality of guide fingers 1922, a handle or hub 1930, and a slotted tubular component 1933. In FIG. 19, the guide fingers 1922 are depicted in a leaflet contact configuration in which a leaflet contact portion 1923 of each guide finger 1922 is configured to be disposed radially within the frame 102 of the transcatheter valve prosthesis 100 and contact an inner surface of the leaflets 105. In the same manner as described above with respect to the guide fingers 222, during crimping of the transcatheter valve prosthesis 100, the plurality of guide fingers 1922 remain disposed radially within the frame 102 such that the leaflets 105 of the valve component 104 preferentially fold around the plurality of guide fingers 1922. The guide fingers 1922 are configured to contact only the inner surfaces of the leaflets 105 of the valve component 104. Stated another way, all of the guide fingers 1922 are radially disposed entirely within the leaflets 105 of the valve component 104 and are configured such that the guide fingers 1922 do not directly contact the outer surface of the leaflets 105 and do not directly contact the frame 102 of the transcatheter valve prosthesis 100.

In an embodiment, when the guide fingers are in the leaflet contact configuration depicted in FIG. 19, each guide finger 1922 extends from the hub 1930 axially and radially outward relative to a longitudinal axis of the transcatheter valve prosthesis 100, and axially and radially outward to a longitudinal axis of the hub 1930. Each guide finger 1922 includes a first end (hidden from view in FIG. 19) that is attached to the hub 1930 and a second end 1926 that is spaced apart from the hub 1930. The second end 926 of each guide finger 1922 is unconstrained, i.e., is free or detached from any other structure. The length of the leaflet contact portion 1923 depends upon the size of the transcatheter valve prosthesis 100 being crimped. As described above with respect to the guide fingers 222, the plurality of guide fingers 1922 include at least three guide fingers. As shown in the embodiment of FIGS. 19-20, the plurality of guide fingers 1922 may include exactly three guide fingers 1922, with each guide finger 1922 being configured to contact a single leaflet 105 of the valve component 104. The guide fingers 1922 may be spring-loaded or shape set into the leaflet contact configuration of FIG. 19.

The hub 1930 of the leaflet folding accessory 1920 is configured to attach to a crimper during use via a plurality of tabs 1937 which would be received within a plurality of mating slots formed on an outer surface of the crimper. When attached to the crimper, the hub 1930 is disposed outside of or external to the crimper, while the slotted tubular component 1933 and guide fingers 1922 are disposed within the crimper chamber of the crimper. The hub 1930 may attach to the crimper adjacent to the inflow portion 106A of the transcatheter valve prosthesis 100, or adjacent to the outflow portion 106C of the transcatheter valve prosthesis 100. The hub 1930 includes a lumen passageway 1955 longitudinally extending therethrough such that the leaflet folding accessory 1920 may be advanced over and relative to an outer surface of a delivery system, on either end (i.e., the outlet or the inlet) of the crimper chamber of the crimper.

The hub 1930 also includes the plurality of slots 1931 formed on an outer surface thereof, and the slotted tubular component 1933 extends axially from the hub 1930. In use during crimping, the slotted tubular component 1933 is positioned over the delivery system and within the central lumen 116 of the transcatheter valve prosthesis. The slotted tubular component 1933 includes a plurality of slots 1935 circumferentially spaced apart from each other at substantially equal intervals. Each slot of the plurality of slots 1931 and each slot of the plurality of slots 1935 are each configured to receive a guide finger 1922. The slots 1931, 1935 provide for controlled radial movement of the guide fingers 1922 during use of the leaflet folding accessory 1920. Particularly, as the transcatheter valve prosthesis 100 is crimped and the guide fingers 1922 radially compress therewith during use, the radial movement of the guide fingers 1922 are controlled by slots 1931 of the hub 1930 until the guide fingers 1922 are positioned into the slots 1935 of the slotted tubular component 1933, as shown in FIG. 20 The guide fingers 1922 radially collapse into the slots 1935 of the slotted tubular component 1933 as the transcatheter valve prosthesis 100 is crimped by the crimper until the transcatheter valve prosthesis 100 is in a partially crimped configuration and disposed over the slotted tubular component 1933. At this stage, the leaflet folding accessory 1920 would be removed from the crimper so that the transcatheter valve 100 may be further crimped to the fully crimped configuration onto the balloon of the delivery system. The slots 1931 of the hub 1930 permit only radial movement of the guide fingers 1922 and do not permit them to move circumferentially (i.e., side or side) during crimping of the transcatheter valve prosthesis 100. Stated another way, the slots 1931 of the hub 1930 permit or allow the guide fingers 1922 to move only a radial direction and not in a circumferential direction. Controlling movement of the guide fingers 1922 may result in a more predictable folding pattern of the leaflets 105 of the transcatheter valve prosthesis 100.

Figure 21:
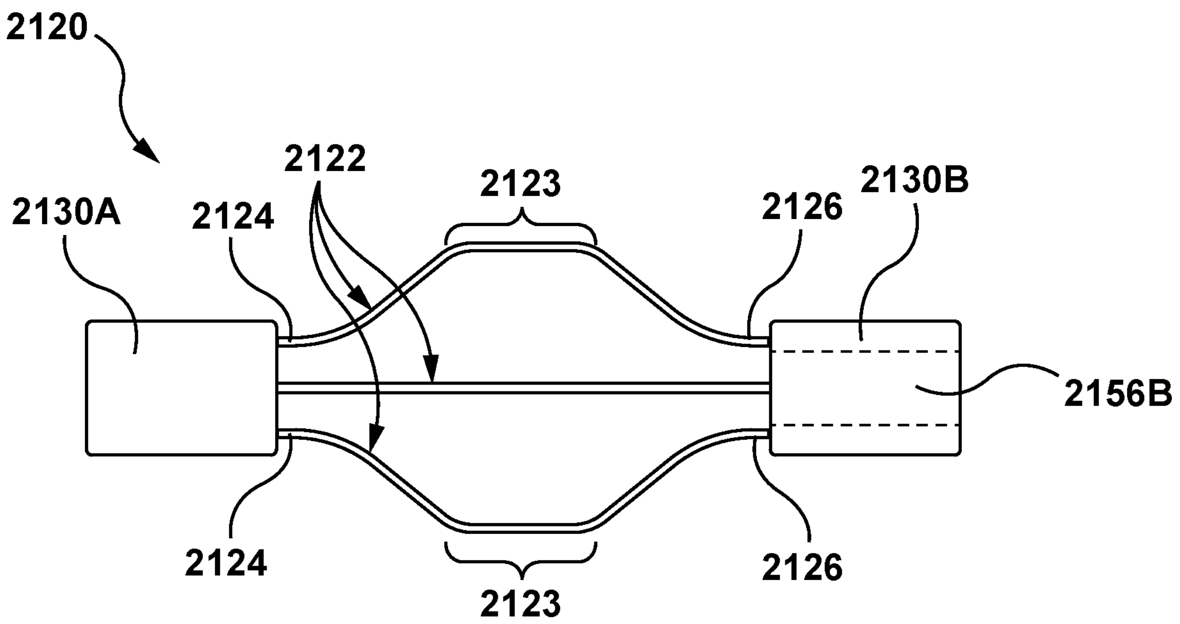
FIG. 21 depicts a side view of a leaflet folding accessory in accordance with another aspect of the disclosure, wherein guide fingers of the leaflet folding accessory are in a leaflet contact configuration and each guide fingers is constrained on opposing ends thereof.
Figure 22:
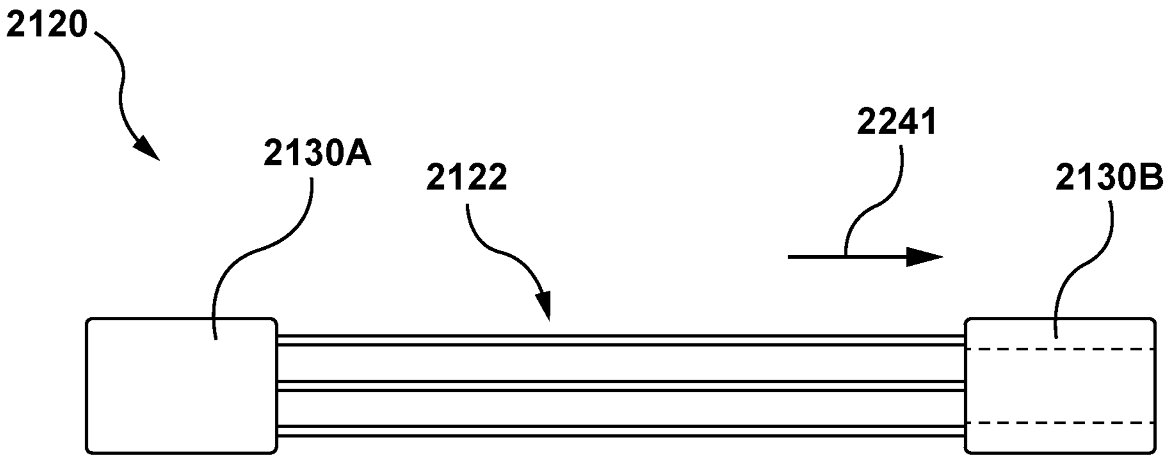
FIG. 22 depicts a side view of the leaflet folding accessory of FIG. 21, wherein the guide fingers of the leaflet folding accessory are radially collapsed.

FIGS. 21 and 22 depict another embodiment of a leaflet folding accessory 2120. FIG. 21 depicts a perspective view of the leaflet folding accessory 2120 with guide fingers 2122 thereof in a leaflet contact configuration while FIG. 22 depicts a perspective view of the leaflet folding accessory 2120 with the guide fingers 2122 is a radially collapsed configuration. In this embodiment, as will be explained in more detail herein, the leaflet folding accessory 2120 includes a first hub 2130A and a second hub 2130B. A first end 2124 of each guide finger 2122 is attached to the first hub 2130A and a second end 2126 of each guide finger 2122 is attached to the second hub 2130B. The second hub 2130B includes a lumen or passageway 2156B longitudinally extending therethrough such that the second hub 2130B may be advanced over and relative to an outer surface of a delivery system. During use, the second hub 2130B slides over the delivery system as the guide fingers 2120 elongate during crimping of the transcatheter valve prosthesis 100.

In FIG. 21, the guide fingers 2122 are depicted in a leaflet contact configuration in which a leaflet contact portion 2123 of each guide finger 2122 is configured to be disposed radially within the frame 102 of the transcatheter valve prosthesis 100 and contact an inner surface of the leaflets 105. In the same manner as described above with respect to the guide fingers 222, during crimping of the transcatheter valve prosthesis 100, the plurality of guide fingers 2122 remain disposed radially within the frame 102 such that the leaflets 105 of the valve component 104 preferentially fold around the plurality of guide fingers 2122. The guide fingers 2122 are configured to contact only the inner surfaces of the leaflets 105 of the valve component 104. Stated another way, all of the guide fingers 2122 are radially disposed entirely within the leaflets 105 of the valve component 104 and are configured such that the guide fingers 2122 do not directly contact the outer surface of the leaflets 105 and do not directly contact the frame 102 of the transcatheter valve prosthesis 100.

When the guide fingers are in the leaflet contact configuration depicted in FIG. 21, each guide finger 2122 has a curved configuration with the first end 2124 of each guide finger 2122 being attached to the first hub 2130A and the second end 2126 of each guide finger 2122 is attached to the second hub 2130B. The guide fingers 2122 may be spring-loaded or shape set into the leaflet contact configuration of FIG. 21, with the leaflet contact portions 2123 forming a generally flat plateau of the curved configuration. The length of the leaflet contact portion 2123 depends upon the size of the transcatheter valve prosthesis 100 being crimped. As described above with respect to the guide fingers 222, the plurality of guide fingers 2122 include at least three guide fingers. As shown in the embodiment of FIG. 21, the plurality of guide fingers 2122 may include exactly three guide fingers 2122, with each guide finger 2122 being configured to contact a single leaflet 105 of the valve component 104.

During use, the first hub 2130A is positioned adjacent to the inflow portion 106A of the transcatheter valve prosthesis 100 within a crimper chamber of a crimper, and the second hub 2130B is positioned adjacent to the outflow portion 106C of the transcatheter valve prosthesis 100 within the crimper chamber of the crimper. The second hub 2130B is positioned over the delivery system via the lumen 2156B, and is configured to slide relative thereto. Particularly, as the transcatheter valve prosthesis 100 is crimped and the guide fingers 2122 radially compress therewith during use, the guide fingers 2122 elongate and second hub 2130B as a result moves in a direction towards the handle of the delivery system, as indicated by directional arrow 2241, until the guide fingers 2122 are substantially straightened as shown in FIG. 22 and the transcatheter valve prosthesis 100 is in a partially crimped configuration. At this stage, the leaflet folding accessory 2120 would be removed from the crimper so that the transcatheter valve 100 may be further crimped to the fully crimped configuration onto the balloon of the delivery system. The leaflet folding accessory 2120 may be removed from the crimper by sliding the leaflet folding accessory 2120 out of the crimper via the inflow portion 106A of the transcatheter valve prosthesis 100. Alternatively, the first hub 2130A may detach from the guide fingers 2122 such that after the transcatheter valve prosthesis 100 is partially crimped, the first hub 2130A may be detached and the guide fingers 2122 may be removed from the crimper by sliding only the guide fingers 2122 out of the crimper via the outflow portion 106C of the transcatheter valve prosthesis 100.

Although described above with only the second hub 2130B be configured to slide over the delivery system during crimping of the transcatheter valve prosthesis 100, the first hub 2130A may also include a lumen of passageway formed therethrough for placement over the delivery system and the first hub 2130A and/or the second hub 2130B may slide relative to the delivery system as the guide fingers 2122 transform from their curved configurations of FIG. 21 to their substantially straight configurations of FIG. 22.

Figure 23:
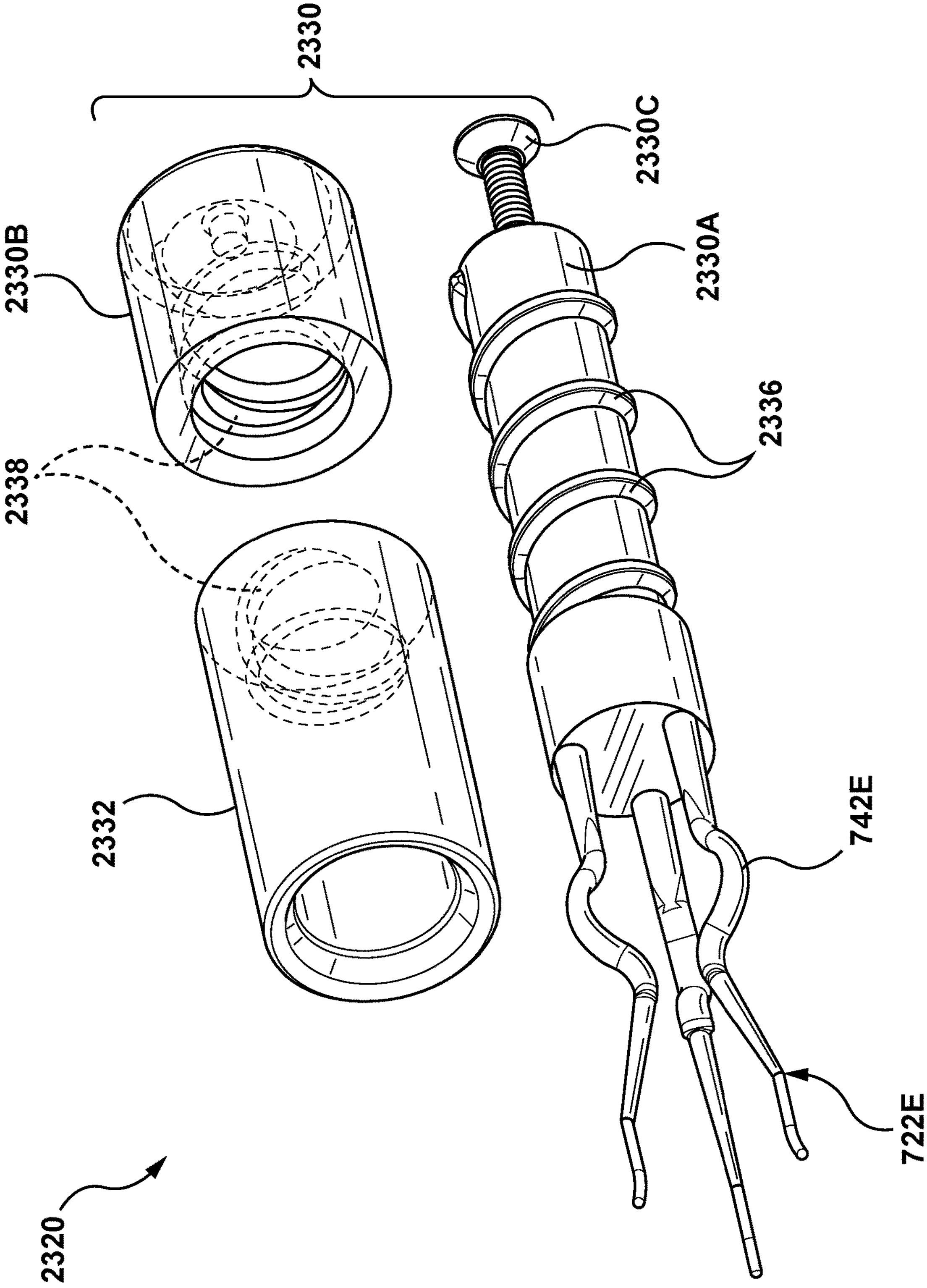
FIG. 23 depicts an exploded perspective view of a leaflet folding accessory according to another embodiment hereof, wherein guide fingers of the leaflet folding accessory are in a leaflet contact configuration and wherein the leaflet folding accessory includes an alternative handle configuration.

The leaflet folding accessories described herein may include alternative handle configurations and are not limited to the configurations of the handle 230 and the rotatable collar 232 described above. FIG. 23 is an exploded perspective view of a leaflet folding accessory 2320 that includes a handle 2330 and a rotatable collar 2332 according to another embodiment hereof. The leaflet folding accessory 2320 includes a plurality of guide fingers 722E, the handle 2330, and the rotatable collar 2332. The guide fingers 722E are the same as the guide finger 722E described above. In FIG. 23, the guide fingers 722E are depicted in a leaflet contact configuration in which a leaflet contact portion of each guide finger 722E is configured and sized to be disposed radially within the frame 102 of the transcatheter valve prosthesis 100 and contact an inner surface of the leaflets 105. Each guide finger 722E extends from the handle 2330 axially and substantially parallel to a longitudinal axis of the handle 2330, and axially and substantially parallel to a longitudinal axis of the transcatheter valve prosthesis 100 when in use.

The handle 2330 is configured to be hand-held by a user in order to position the leaflet folding accessory 2320 as desired during the crimping process of the transcatheter valve prosthesis 100. The handle 2330 includes a first concentric portion 2330A and a second concentric portion 2330B. The first concentric portion 2330A includes a first threaded surface 2336 having a first plurality of threads formed or disposed on an outer surface thereof. The second concentric portion 2330B includes a second threaded surface 2338 having a second plurality of threads formed on an inner surface thereof. The threads of the first threaded surface 2336 are configured to mate with the threads of the second threaded surface 2338. When assembled, the second concentric portion 2330B is disposed over the first concentric portion 2330A and secured to the first concentric portion 2330A via a fastener 2330C. Via the fastener 2330C, the first concentric portion 2330A and the second concentric portion 2330B are attached or secured to each other such that relative rotation therebetween is not permitted. Stated another way, the fastener 2330C, the first concentric portion 2330A and the second concentric portion 2330B form a subassembly and no relative movement is permitted once assembled together.

The collar 2332 is also configured to be disposed over the first concentric portion 2330A of the handle 2330 after assembly. More particularly, the collar 2332 also includes the second threaded surface 2338. As described above, the second threaded surface 2338 has a second plurality of threads formed on an inner surface thereof that are configured to mate with the threads of the first threaded surface 2386. Once assembled onto the handle 2330, the collar 2332 is disposed closer to the guide fingers 722E than the second concentric portion 2330B. After assembly onto the handle 2330, the collar 2332 is configured to rotate relative to the handle 2330, or more specifically, to the first concentric portion 2330A of the handle 2330.

The collar 2332 is rotatable relative to the handle 2330 in order to adjust a radial position of the leaflet contact portions of the guide fingers 722E. More particularly, the leaflet contact portions of the guide fingers 722E may be radially compressed for easy insertion into the transcatheter valve prosthesis 100. After the guide fingers 722E are in the correct longitudinal position within the transcatheter valve prosthesis 100, the guide fingers 722E may be radially expanded to resume the leaflet contact configuration and thereby contact the leaflets 105 such that each guide finger 722E is positioned to hold at least a portion of a leaflet 105 of the transcatheter valve prosthesis 100 directly adjacent to or against an inner surface of the frame 105 of the transcatheter valve prosthesis 100. When the collar 2332 is rotated in a first direction, i.e., counter clockwise or clockwise depending on the direction of the threads, the collar 2332 moves in a longitudinal direction towards the guide fingers 722E due to the interaction between the mating first and second threaded surface 2336, 2338. As the collar 2332 moves longitudinally, the collar 2332 moves into contact with the outward bumps 742E formed on the guide fingers 722E and the leaflet contact portions of the guide fingers 722E are deflected or moved radially inward. When deflected radially inwards, the leaflet contact portions may be easily positioned into the frame 102 of the transcatheter valve prosthesis 100. Once positioned as desired, a user may rotate the collar 2332 in a second direction that opposes the first direction, i.e., the other of counter clockwise or clockwise, to cause the collar 2332 to move back to its initial longitudinal position and permit the guide fingers 722E to resume or revert to their initial radial positions of the leaflet contact configuration.

Advantageously, for the embodiment of FIG. 23, assembly of the components of the leaflet folding accessory 2320 does not require the guide fingers 722E to be radially compressed. More particularly, the rotatable collar 2332 and the second concentric portion 2330B can be threaded onto the first concentric portion 2330A from the end opposite from the guide fingers 722E. As such, the guide fingers 722E do not need to be compressed during assembly and can remain in their leaflet contact configuration during assembly of the rotatable collar 2332 and the second concentric portion 2330B onto the first concentric portion 2330A.

Figure 24:
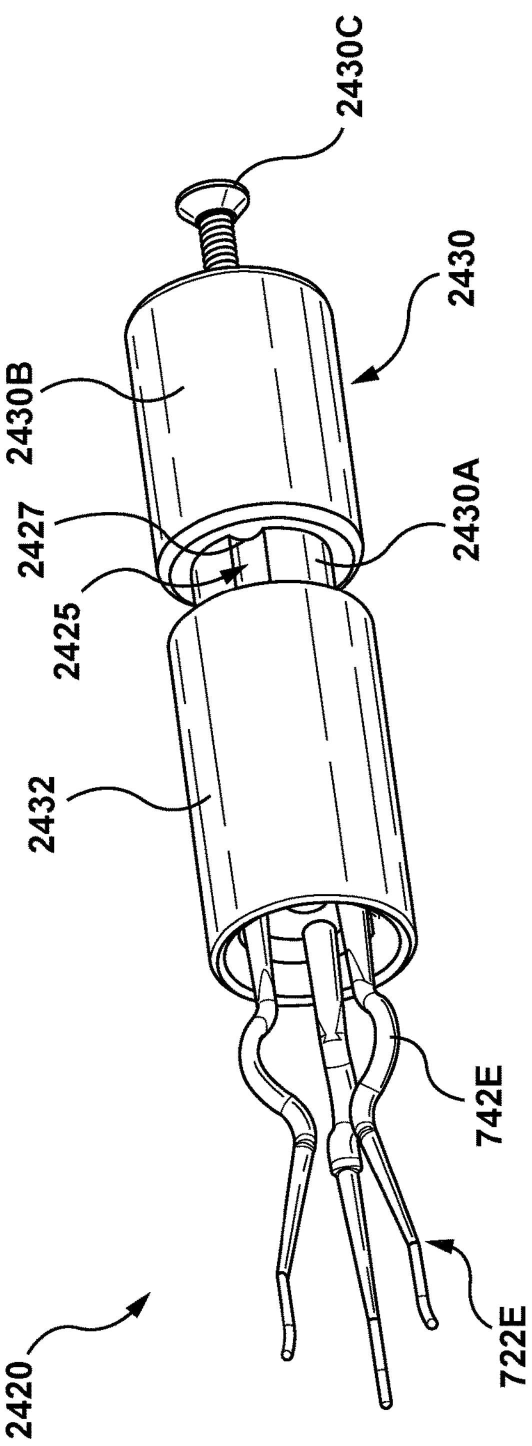
FIG. 24 depicts a perspective view of a leaflet folding accessory according to another embodiment hereof, wherein guide fingers of the leaflet folding accessory are in a leaflet contact configuration and wherein the leaflet folding accessory includes a slidable collar.
Figure 25:
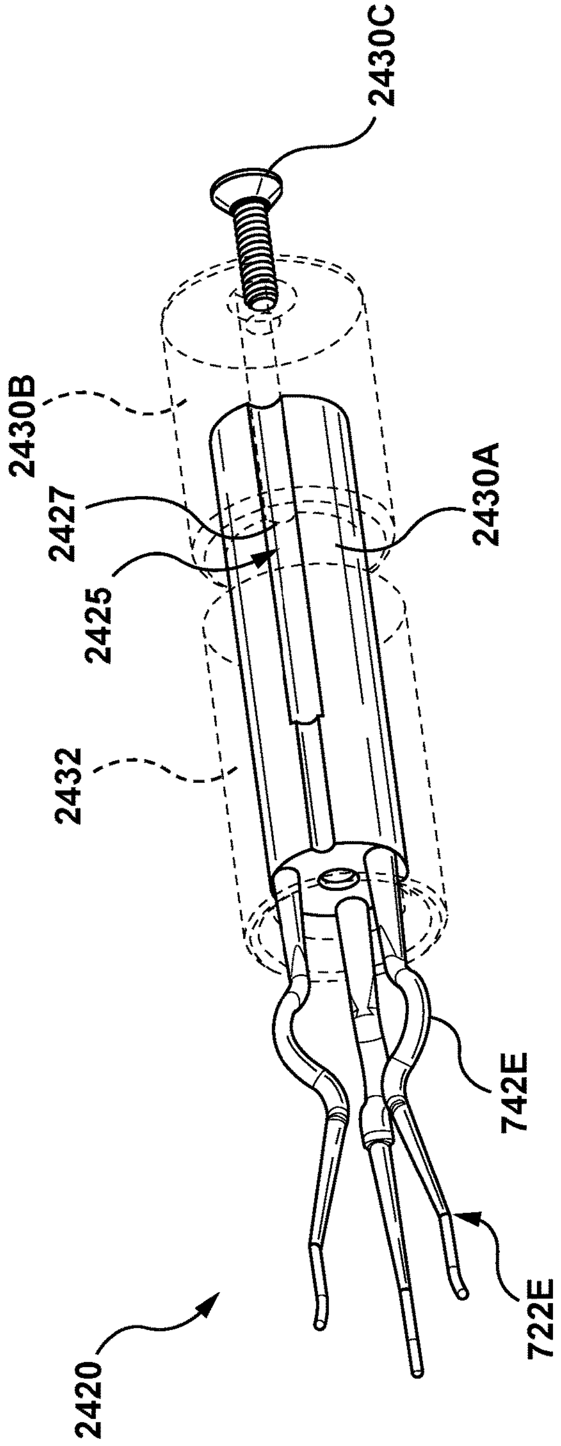
FIG. 25 depicts a perspective view of the leaflet folding accessory of FIG. 24, wherein the slidable collar and a second concentric portion of a handle are shown in phantom.
Figure 26:
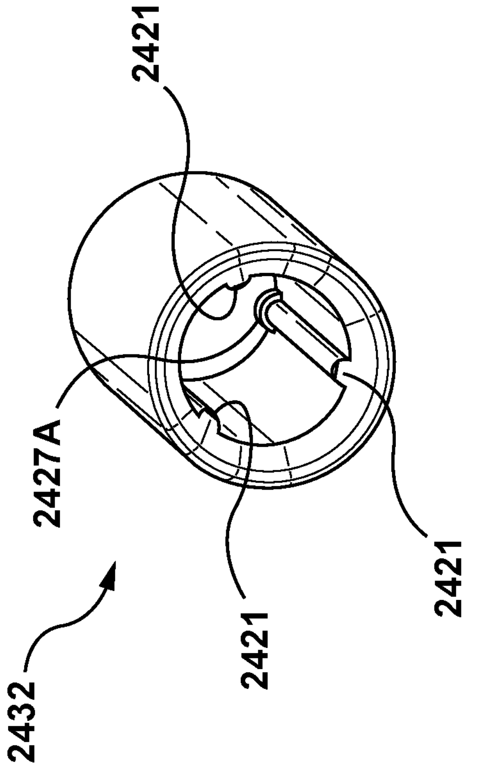
FIG. 26 depicts a perspective view of the slidable collar of the leaflet folding accessory of FIG. 24, wherein the slidable collar is shown removed from the leaflet folding accessory for sake of illustration only.
Figure 27:
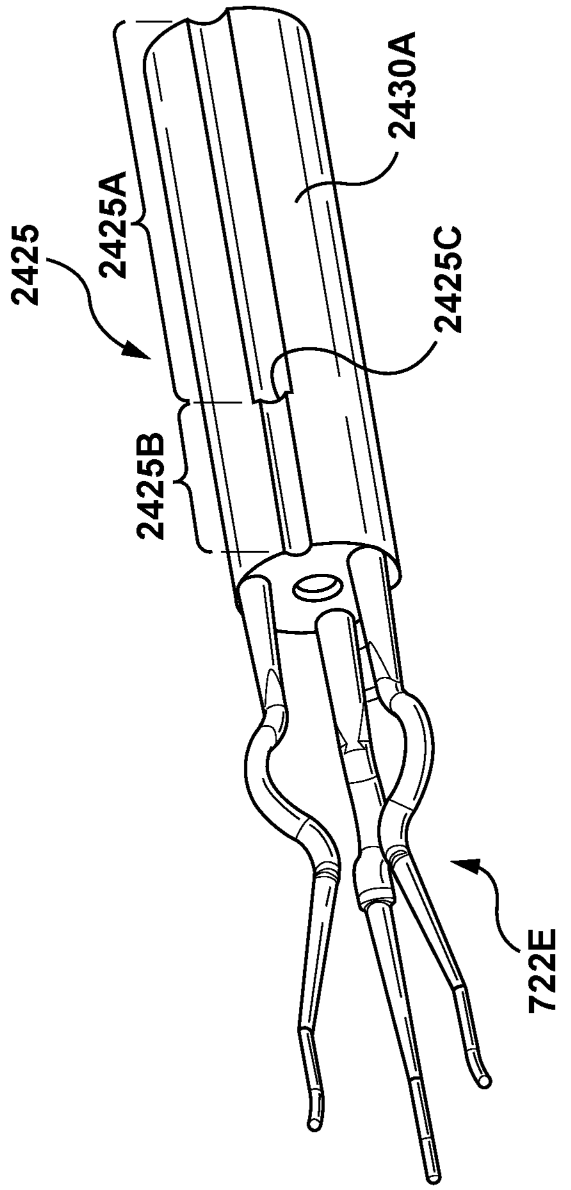
FIG. 27 depicts a perspective view of a first concentric portion of the handle of the leaflet folding accessory of FIG. 24, wherein the first concentric portion is shown removed from the leaflet folding accessory for sake of illustration only.

An alternative handle embodiment which utilizes a slidable collar rather than a rotatable collar is depicted in FIGS. 24-27. In some instances, a slidable collar may be preferred over a rotatable collar due to ergonomic considerations and/or personal user preference. FIG. 24 is a perspective view of a leaflet folding accessory 2420 that includes a slidable collar 2432 according to another embodiment hereof. The leaflet folding accessory 2420 includes a plurality of guide fingers 722E, a handle 2430, and the slidable collar 2432. The guide fingers 722E are the same as the guide finger 722E described above. In FIG. 24, the guide fingers 722E are depicted in a leaflet contact configuration in which a leaflet contact portion of each guide finger 722E is configured and sized to be disposed radially within the frame 102 of the transcatheter valve prosthesis 100 and contact an inner surface of the leaflets 105. Each guide finger 722E extends from the handle 2430 axially and substantially parallel to a longitudinal axis of the handle 2430, and axially and substantially parallel to a longitudinal axis of the transcatheter valve prosthesis 100 when in use.

The handle 2430 is configured to be hand-held by a user in order to position the leaflet folding accessory 2420 as desired during the crimping process of the transcatheter valve prosthesis 100. The handle 2430 includes a first concentric portion 2430A and a second concentric portion 2430B. The first concentric portion 2430A of the handle 2430 includes at least one elongated channel or groove 2425 formed or disposed on an outer surface thereof. Although obscured from view, in this embodiment, the first concentric portion 2430A includes three grooves 2425 equally spaced around a circumference of the first concentric portion 2430A. With additional reference to FIG. 27, each elongated channel or groove 2425 includes a first longitudinal portion 2425A and a second longitudinal portion 2425B in which the size of the groove is smaller or reduced. A stepped surface 2425C is formed between the first and second longitudinal portions 2425A, 2425B. The second concentric portion 2430B of the handle 2430 includes at least one elongated rib 2427 formed on an inner surface thereof. Although obscured from view, in this embodiment, the second concentric portion 2430B includes three ribs 2427 equally spaced around the inner circumferential surface thereof. Each elongated rib 2427 is configured or sized to be received within the first longitudinal portion 2425A of the groove 2425 such that that the second concentric portion 2430B may slide over the first concentric portion 2430A during assembly. When assembled, the second concentric portion 2430B is disposed over the first concentric portion 2430A and secured to the first concentric portion 2430A via a fastener 2430C. Via the fastener 2430C, the first concentric portion 2430A and the second concentric portion 2430B are attached or secured to each other such that relative rotation therebetween is not permitted. Stated another way, the fastener 2430C, the first concentric portion 2430A and the second concentric portion 2430B form a subassembly and no relative movement is permitted once assembled together.

The collar 2432 is also configured to be disposed over the first concentric portion 2430A of the handle 2430 after assembly. More particularly, with additional reference to FIG. 26, the collar 2432 includes at least one elongated rib 2421 formed on an inner surface thereof. In this embodiment, the collar 2432 includes three ribs 2421 equally spaced around the inner circumferential surface thereof. The elongated rib 2421 includes a flange 2427A at an end thereof in which the size of the rib is increased. More particularly, the size or configuration of the flange 2427A is the same as the size or configuration of the elongated rib 2427 of the second concentric portion 2340B. Except for the flange 2427A, the elongated rib 2421 is configured or sized to be received within the second longitudinal portion 2425B of the groove 2425. Once assembled onto the handle 2430, the collar 2432 is disposed closer to the guide fingers 722E than the second concentric portion 2430B. After assembly onto the handle 2430, the collar 2432 is configured to slide or move axially/longitudinally relative to the handle 2430, or more specifically, to the first concentric portion 2430A of the handle 2430.

The collar 2432 is slidable relative to the handle 2430 in order to adjust a radial position of the leaflet contact portions of the guide fingers 722E. More particularly, the leaflet contact portions of the guide fingers 722E may be radially compressed for easy insertion into the transcatheter valve prosthesis 100. After the guide fingers 722E are in the correct longitudinal position within the transcatheter valve prosthesis 100, the guide fingers 722E may be radially expanded to resume the leaflet contact configuration and thereby contact the leaflets 105 such that each guide finger 722E is positioned to hold at least a portion of a leaflet 105 of the transcatheter valve prosthesis 100 directly adjacent to or against an inner surface of the frame 105 of the transcatheter valve prosthesis 100. When the collar 2432 is translated or moved in a longitudinal direction towards the guide fingers 722E, the collar 2432 moves into contact with the outward bumps 742E formed on the guide fingers 722E and the leaflet contact portions of the guide fingers 722E are deflected or moved radially inward. When deflected radially inwards, the leaflet contact portions may be easily positioned into the frame 102 of the transcatheter valve prosthesis 100. Longitudinal translation of the collar 2432 is limited by interaction between the flange 2427A of the collar 2432 and the stepped surface 2425C of the groove 2425. More particularly, axial or longitudinal movement of the collar 2432 in the direction towards the guide fingers 722E is prohibited after the flange 2427A of the collar 2432 abuts against the stepped surface 2425C. Once the guide fingers 722E are positioned as desired within the transcatheter valve prosthesis 100, a user may translate or move the collar 2432 in a longitudinal direction away from the guide fingers 722E to cause the collar 2432 to move back to its initial longitudinal position and permit the guide fingers 722E to resume or revert to their initial radial positions of the leaflet contact configuration.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. An assembly comprising:

a transcatheter valve prosthesis including a frame and a prosthetic valve component including at least one leaflet disposed within and secured to the frame, the transcatheter valve prosthesis having an expanded configuration and a crimped configuration for delivery within a vasculature;

a leaflet folding accessory configured for use when compressing the transcatheter valve prosthesis into the crimped configuration, the leaflet folding accessory including a plurality of guide fingers, wherein all guide fingers of the leaflet folding accessory includes a leaflet contact portion which is configured to be disposed radially within the frame and contact an inner surface of a leaflet of the at least one leaflet and configured to not directly contact an outer surface of the leaflet, wherein, during crimping of the transcatheter valve prosthesis, the plurality of guide fingers are configured to remain disposed radially within the frame such that the at least one leaflet preferentially folds around the plurality of guide fingers, and wherein the leaflet folding accessory includes a handle configured to be held by a user, the handle being attached to a first end of each guide finger, and wherein the leaflet folding accessory further includes a collar disposed over the handle, the collar being moveable relative to the guide fingers in order to adjust a radial position of the leaflet contact portions of the guide fingers.

2. The assembly of claim 1, wherein the plurality of guide fingers include at least three guide fingers.

3. The assembly of claim 2, wherein the plurality of guide fingers include exactly three guide fingers and the prosthetic valve component includes exactly three leaflets.

4. The assembly of claim 1, wherein each guide finger is formed of a pliable polymer material.

5. The assembly of claim 1, wherein the plurality of guide fingers are circumferentially spaced apart from each other.

6. The assembly of claim 1, wherein the leaflet folding accessory includes a handle configured to be held by a user, the handle being attached to a first end of each guide finger.

7. The assembly of claim 1, wherein the leaflet contact portion of each guide finger is a curved end portion.

8. The assembly of claim 1, wherein each guide finger is a rod having a substantially circular cross section.

9. The assembly of claim 8, wherein each guide finger tapers from a first end to a second end thereof, the first end having a greater diameter than the second end.

10. The assembly of claim 1, wherein each guide finger has a flattened, ribbon-like cross section.

11. The assembly of claim 1, wherein the leaflet folding accessory includes a handle configured to be held by a user and wherein a first end of each guide finger is attached to a nut, the nut being removably attached to an end of the handle.

12. The assembly of claim 1, wherein the assembly further includes a valve seat locator configured to receive an end of the transcatheter valve prosthesis, the valve seat locator being configured to align the leaflet contact portion of each guide finger with a midline of the at least one leaflet.

13. The assembly of claim 1, wherein the leaflet folding accessory includes a hub, the hub being attached to a first end of each guide finger, and a second end of each guide finger is unconstrained.

14. The assembly of claim 1, wherein each guide finger includes an outward bump formed on a midportion thereof, the outward bump extending radially outward and being configured to interact with the collar.

15. An assembly comprising:

a transcatheter valve prosthesis including a frame and a prosthetic valve component including at least one leaflet disposed within and secured to the frame, the transcatheter valve prosthesis having an expanded configuration and a crimped configuration for delivery within a vasculature;

a leaflet folding accessory configured for use when compressing the transcatheter valve prosthesis into the crimped configuration, the leaflet folding accessory including a plurality of guide fingers, wherein a leaflet contact portion of each guide finger is configured to be disposed radially within the frame and contact an inner surface of a leaflet of the at least one leaflet, wherein the leaflet folding accessory also includes a handle configured to be held by a user, the handle being attached to a first end of each guide finger, and wherein the leaflet folding accessory further includes a collar disposed over the handle, the collar being moveable relative to the guide fingers in order to adjust a radial position of the leaflet contact portions of the guide fingers, wherein, during crimping of the transcatheter valve prosthesis, the plurality of guide fingers are configured to remain disposed radially within the frame such that the at least one leaflet preferentially folds around the plurality of guide fingers.

16. The assembly of claim 15, wherein each guide finger includes an outward bump formed on a midportion thereof, the outward bump extending radially outward and being configured to interact with the collar.

* * * * *